(12) United States Patent
Shaolian et al.

(10) Patent No.: US 6,733,523 B2
(45) Date of Patent: May 11, 2004

(54) IMPLANTABLE VASCULAR GRAFT

(75) Inventors: Samuel M. Shaolian, Newport Beach, CA (US); Frank M. Zeng, Irvine, CA (US)

(73) Assignee: Endologix, Inc., Irvine, CA (US)

( * ) Notice: Subject to any disclaimer, the term of this patent is extended or adjusted under 35 U.S.C. 154(b) by 0 days.

(21) Appl. No.: 09/891,620

(22) Filed: Jun. 26, 2001

(65) Prior Publication Data

US 2002/0052644 A1 May 2, 2002

Related U.S. Application Data

(63) Continuation-in-part of application No. 09/728,582, filed on Dec. 1, 2000, which is a continuation-in-part of application No. 09/251,363, filed on Feb. 17, 1999, now Pat. No. 6,197,049, which is a continuation-in-part of application No. 09/210,280, filed on Dec. 11, 1998, now Pat. No. 6,187,036.

(51) Int. Cl.$^7$ .................................................. A61F 2/06
(52) U.S. Cl. ..................... 623/1.35; 623/623; 623/1.27; 623/1.3
(58) Field of Search ............................... 623/1.13, 1.14, 623/1.15–1.18, 1.2, 1.35

(56) References Cited

U.S. PATENT DOCUMENTS

| 519,928 A | 5/1894 | Schanck |
|---|---|---|
| 1,065,935 A | 7/1913 | Gail |
| 2,127,903 A | 8/1938 | Bowen |
| 2,437,542 A | 3/1948 | Krippendorf |
| 2,845,959 A | 8/1958 | Sidebotham |
| 2,990,605 A | 7/1961 | Demsyk |
| 3,029,819 A | 4/1962 | Starks |
| 3,096,560 A | 7/1963 | Liebig |
| 3,805,301 A | 4/1974 | Liebig |
| 4,497,074 A | 2/1985 | Rey et al. |
| 4,501,263 A | 2/1985 | Harbuck |
| 4,503,568 A | 3/1985 | Madras |
| 4,592,754 A | 6/1986 | Gupte et al. |
| 4,617,932 A | 10/1986 | Kornberg |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,922,905 A | 5/1990 | Strecker |
| 4,981,478 A | 1/1991 | Evard et al. |
| 4,994,071 A | 2/1991 | MacGregor |
| 5,019,090 A | 5/1991 | Pinchuk |
| 5,064,435 A | 11/1991 | Porter |
| 5,078,726 A | 1/1992 | Kreamer |
| 5,104,399 A | 4/1992 | Lazarus |
| 5,108,424 A | 4/1992 | Hoffman, Jr. et al. |

(List continued on next page.)

FOREIGN PATENT DOCUMENTS

| DE | 295 21 548 U1 | 2/1995 |
|---|---|---|
| DE | 295 21 776 U1 | 2/1995 |
| EP | 458 568 A1 | 5/1991 |

(List continued on next page.)

OTHER PUBLICATIONS

PCT Written Opinion dated Sep. 13, 2001.

*Primary Examiner*—Corrine McDermott
*Assistant Examiner*—Hieu Phan
(74) *Attorney, Agent, or Firm*—Knobbe, Martens, Olson & Bear, LLP.

(57) ABSTRACT

Disclosed is a tubular endoluminal vascular prosthesis, useful in treating, for example, an abdominal aortic aneurysm. The prosthesis comprises a self-expandable wire support structure having a tubular main body support and first and second branch supports. The support structure may include sliding links to permit flexibility while maintaining patency of the central lumen. The branch supports may articulate with the main body to permit the branches to pivot laterally from the axis of the main body throughout a substantial range of motion. Exoskeleton components or barbs may be provided to resist migration and endoleaks.

35 Claims, 28 Drawing Sheets

U.S. PATENT DOCUMENTS

| | | |
|---|---|---|
| 5,123,917 A | 6/1992 | Lee |
| 5,133,732 A * | 7/1992 | Wiktor ..................... 604/104 |
| 5,135,536 A | 8/1992 | Hillstead |
| 5,156,619 A | 10/1992 | Ehrenfeld |
| 5,178,634 A | 1/1993 | Ramos Martinez |
| 5,197,976 A | 3/1993 | Herweck et al. |
| 5,201,757 A | 4/1993 | Heyn et al. |
| 5,256,141 A | 10/1993 | Gencheff et al. |
| 5,275,622 A | 1/1994 | Lazarus et al. |
| 5,282,824 A | 2/1994 | Gianturco |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpiel |
| 5,330,500 A | 7/1994 | Song |
| 5,342,387 A | 8/1994 | Summers |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,387,235 A | 2/1995 | Chuter |
| 5,397,355 A | 3/1995 | Marin et al. |
| 5,405,377 A | 4/1995 | Cragg |
| 5,423,886 A | 6/1995 | Arru et al. |
| 5,425,765 A | 6/1995 | Tiefenbrun et al. |
| 5,443,498 A | 8/1995 | Fontaine |
| 5,443,500 A | 8/1995 | Sigwart |
| 5,456,713 A | 10/1995 | Chuter |
| 5,458,615 A | 10/1995 | Klemm et al. |
| 5,462,530 A | 10/1995 | Jang |
| 5,464,450 A | 11/1995 | Buscemi et al. |
| 5,484,444 A | 1/1996 | Braunschweiler et al. |
| 5,489,295 A | 2/1996 | Piplani et al. |
| 5,496,365 A | 3/1996 | Sgro |
| 5,507,767 A | 4/1996 | Maeda et al. |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,545,211 A | 8/1996 | An et al. |
| 5,554,118 A | 9/1996 | Jang |
| 5,554,181 A | 9/1996 | Das |
| 5,562,726 A | 10/1996 | Chuter |
| 5,562,728 A | 10/1996 | Lazarus et al. |
| 5,571,173 A | 11/1996 | Parodi |
| 5,575,816 A | 11/1996 | Rudnick et al. |
| 5,575,818 A | 11/1996 | Pinchuk |
| 5,578,072 A | 11/1996 | Barone et al. |
| 5,591,197 A | 1/1997 | Orth et al. |
| 5,591,198 A | 1/1997 | Boyle et al. |
| 5,591,229 A | 1/1997 | Parodi |
| 5,591,230 A | 1/1997 | Horn et al. |
| 5,593,417 A | 1/1997 | Rhodes |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,783 A | 5/1997 | Quiachon et al. |
| 5,628,788 A | 5/1997 | Pinchuk |
| 5,630,829 A | 5/1997 | Lauterjung |
| 5,632,772 A | 5/1997 | Alcime et al. |
| 5,639,278 A | 6/1997 | Dereume et al. |
| 5,641,373 A | 6/1997 | Shannon et al. |
| 5,643,339 A | 7/1997 | Kavteladze et al. |
| 5,647,857 A | 7/1997 | Anderson et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,614 A | 9/1997 | Edoga |
| 5,662,700 A | 9/1997 | Lazarus |
| 5,662,702 A | 9/1997 | Keranen |
| 5,662,703 A | 9/1997 | Yurek et al. |
| 5,662,728 A | 9/1997 | Groeger |
| 5,665,115 A | 9/1997 | Cragg |
| 5,665,117 A | 9/1997 | Rhodes |
| 5,669,880 A | 9/1997 | Solar |
| 5,669,924 A | 9/1997 | Shaknovich |
| 5,674,241 A | 10/1997 | Bley et al. |
| 5,674,276 A | 10/1997 | Andersen et al. |
| 5,676,696 A | 10/1997 | Marcade |
| 5,676,697 A | 10/1997 | McDonald |
| 5,679,400 A | 10/1997 | Tuch |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,776 A | 2/1998 | Chuter et al. |
| 5,723,004 A | 3/1998 | Dereume et al. |
| 5,733,325 A | 3/1998 | Robinson et al. |
| 5,746,766 A | 5/1998 | Edoga |
| 5,749,880 A | 5/1998 | Banas et al. |
| 5,755,770 A | 5/1998 | Ravenscroft |
| 5,755,771 A | 5/1998 | Penn et al. |
| 5,769,885 A | 6/1998 | Quiachon et al. |
| 5,769,887 A | 6/1998 | Brown et al. |
| 5,782,909 A | 7/1998 | Quiachon et al. |
| 5,800,456 A | 9/1998 | Maeda et al. |
| 5,800,508 A | 9/1998 | Goicoechea et al. |
| 5,810,836 A | 9/1998 | Hussein et al. |
| 5,824,037 A | 10/1998 | Fogarty et al. |
| 5,824,039 A | 10/1998 | Piplani et al. |
| 5,824,053 A | 10/1998 | Khosravi et al. |
| 5,843,160 A | 12/1998 | Rhodes |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,860,998 A | 1/1999 | Robinson et al. |
| 5,868,783 A | 2/1999 | Tower |
| 5,879,321 A | 3/1999 | Hill |
| 5,879,366 A | 3/1999 | Shau et al. |
| 5,891,193 A | 4/1999 | Robinson et al. |
| 5,893,887 A | 4/1999 | Jayaraman |
| 5,902,334 A | 5/1999 | Dwyer et al. |
| 5,906,640 A | 5/1999 | Penn et al. |
| 5,916,263 A | 6/1999 | Goicoeceha et al. |
| 5,919,225 A * | 7/1999 | Lau et al. ..................... 606/108 |
| 5,925,075 A * | 7/1999 | Myers et al. ................ 606/198 |
| 5,928,279 A | 7/1999 | Shannon et al. |
| 5,935,161 A | 8/1999 | Robinson et al. |
| 5,938,696 A | 8/1999 | Goicoechea et al. |
| 5,948,018 A | 9/1999 | Dereume et al. |
| 5,957,973 A | 9/1999 | Quiachon et al. |

| | | | | | | |
|---|---|---|---|---|---|---|
| 5,961,546 | A | 10/1999 | Robinson et al. | EP | 323 176 B1 | 3/1994 |
| 5,961,548 | A | 10/1999 | Shmulewitz | EP | 0 596 145 A1 | 5/1994 |
| 6,004,347 | A | 12/1999 | McNamara et al. | EP | 0 621 015 A1 | 10/1994 |
| 6,004,348 | A | 12/1999 | Banas et al. | EP | 782 841 A2 | 2/1995 |
| 6,017,363 | A | 1/2000 | Hojeibane | EP | 783 873 A2 | 2/1995 |
| 6,027,779 | A | 2/2000 | Campbell et al. | EP | 783 874 A2 | 2/1995 |
| 6,027,811 | A | 2/2000 | Campbell et al. | EP | 659 389 A1 | 6/1995 |
| 6,030,415 | A | 2/2000 | Chuter | EP | 0 659 389 A1 | 6/1995 |
| 6,039,749 | A | 3/2000 | Marin et al. | EP | 689 806 A2 | 1/1996 |
| 6,039,755 | A | 3/2000 | Edwin et al. | EP | 747 020 A2 | 2/1996 |
| 6,051,020 | A | 4/2000 | Goicoechea et al. | EP | 732 089 A3 | 3/1996 |
| 6,070,589 | A | 6/2000 | Keith et al. | EP | 712 614 A1 | 5/1996 |
| 6,074,398 | A | 6/2000 | Leschinsky | EP | 732 088 A3 | 9/1996 |
| 6,077,296 | A | 6/2000 | Shokooji et al. | EP | 740 928 A2 | 11/1996 |
| 6,077,297 | A | 6/2000 | Robinson et al. | EP | 0 740 928 A2 | 11/1996 |
| 6,106,548 | A | 8/2000 | Reubin et al. | EP | 0 747 020 A2 | 12/1996 |
| 6,117,167 | A | 9/2000 | Goicoechea et al. | EP | 732 089 A3 | 2/1997 |
| 6,123,722 | A | 9/2000 | Fogarty et al. | EP | 0 775 470 A1 | 5/1997 |
| 6,123,723 | A | 9/2000 | Konya et al. | EP | 775 470 A1 | 5/1997 |
| 6,126,685 | A | 10/2000 | Lenker et al. | EP | 0 880 948 A1 * | 1/1998 |
| 6,129,756 | A | 10/2000 | Kugler et al. | EP | 880 948 A1 | 5/1998 |
| 6,168,610 | B1 | 1/2001 | Marin et al. | EP | 880 938 A1 | 12/1998 |
| 6,183,481 | B1 | 2/2001 | Lee et al. | EP | 0 904 745 A2 | 3/1999 |
| 6,187,036 | B1 | 2/2001 | Shaolian et al. | EP | 974 314 A2 | 1/2000 |
| 6,192,944 | B1 | 2/2001 | Greenhalgh | EP | 732 088 B1 | 4/2000 |
| 6,203,735 | B1 | 3/2001 | Edwin et al. | ES | 1 038 606 | 7/1998 |
| 6,273,909 | B1 | 8/2001 | Kugler et al. | JP | 9-511160 | 11/1997 |
| 6,280,466 | B1 | 8/2001 | Kugler et al. | WO | WO 93/13825 | 7/1993 |
| 6,280,467 | B1 | 8/2001 | Leonhardt | WO | WO94/24961 | 2/1994 |
| 6,283,991 | B1 * | 9/2001 | Cox et al. ............ 623/1.13 | WO | WO95/21592 | 2/1995 |
| 6,514,281 | B1 | 2/2003 | Blaeser et al. | WO | WO 96/41589 | 12/1996 |
| 6,517,572 | B2 | 2/2003 | Kugler et al. | WO | WO97/26936 | 1/1997 |
| 6,517,573 | B1 | 2/2003 | Pollock et al. | WO | WO 97/10757 | 3/1997 |
| 6,533,811 | B1 | 3/2003 | Ryan et al. | WO | WO 97/10777 | 3/1997 |
| 2003/0065380 | A1 | 4/2003 | Kugler et al. | WO | WO 97/14375 | 4/1997 |
| 2003/0065385 | A1 | 4/2003 | Weadock | WO | WO 97/19652 | 6/1997 |
| | | | | WO | WO 98/02100 | 1/1998 |
| | | FOREIGN PATENT DOCUMENTS | | WO | WO 99/44536 | 9/1999 |
| EP | | 0 177 330 B1 | 6/1991 | WO | WO 99/47077 | 9/1999 |
| EP | | 282 175 B1 | 11/1991 | WO | WO 99/58084 | 11/1999 |
| EP | | 596 145 A1 | 10/1992 | | | |
| EP | | 621 015 A1 | 4/1993 | * cited by examiner | | |

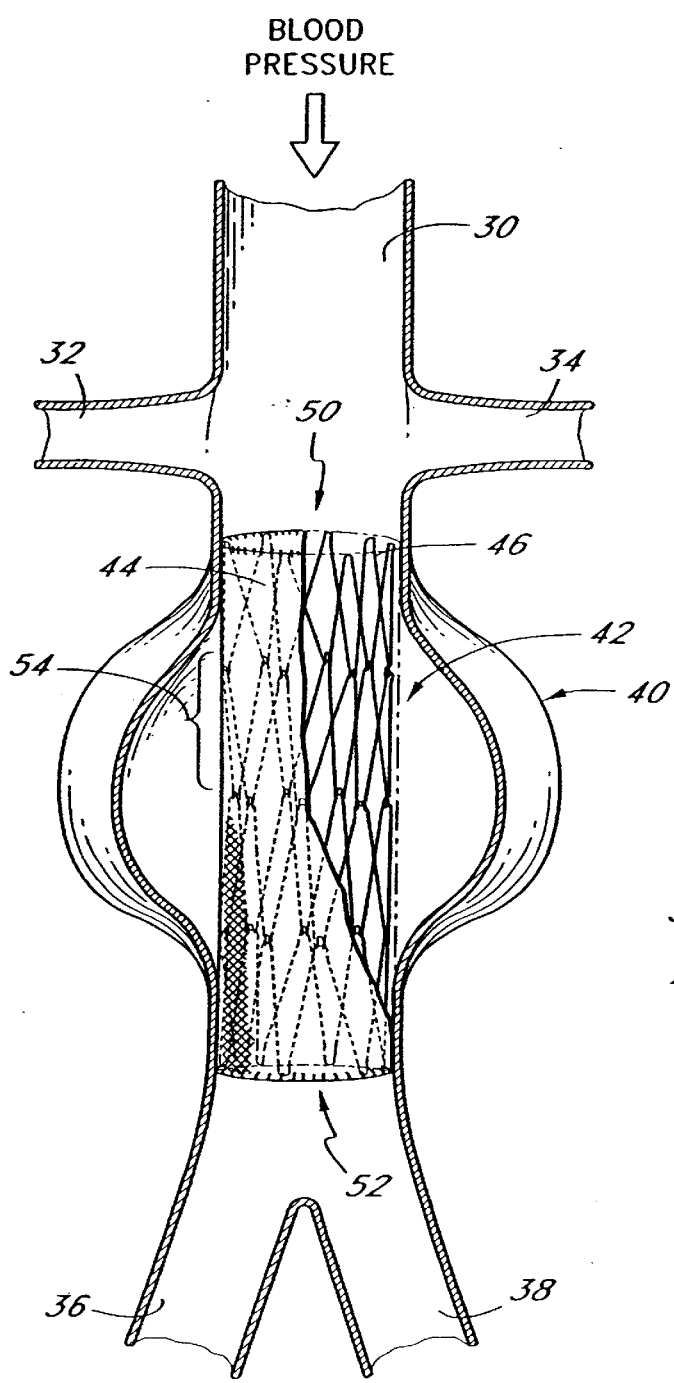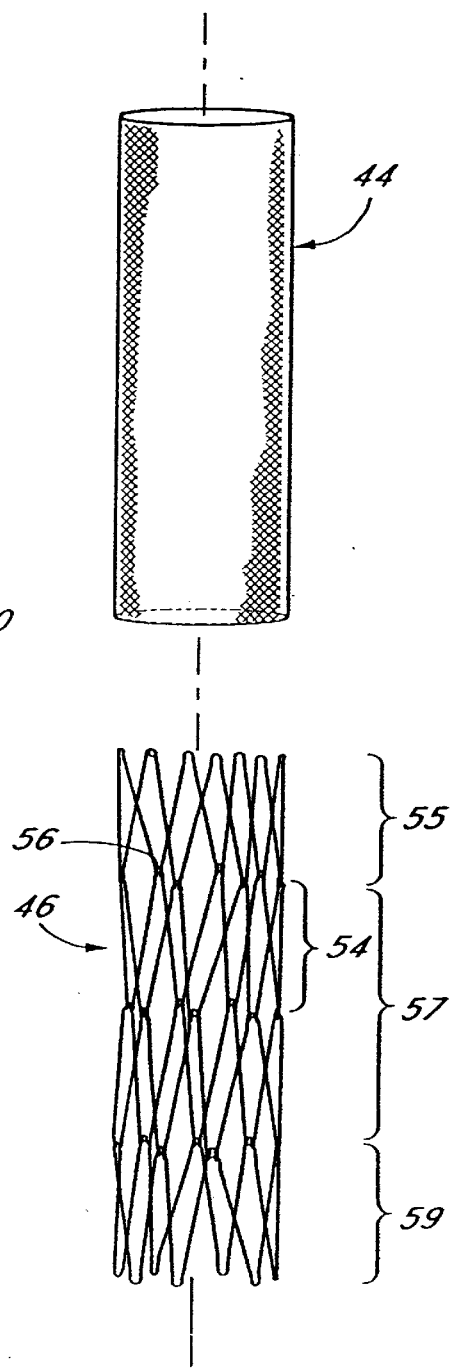

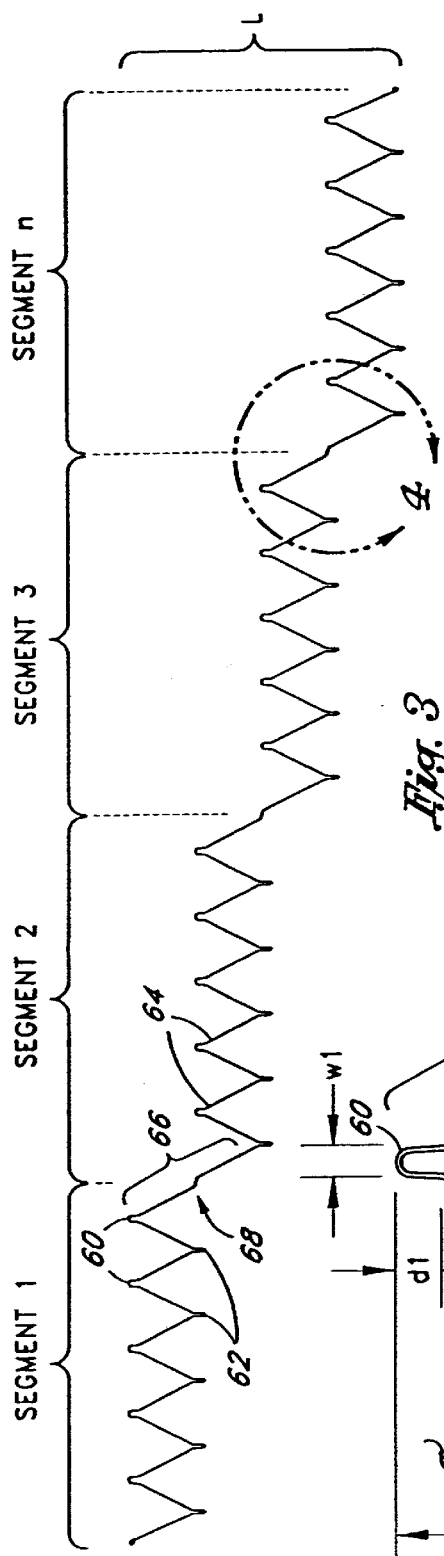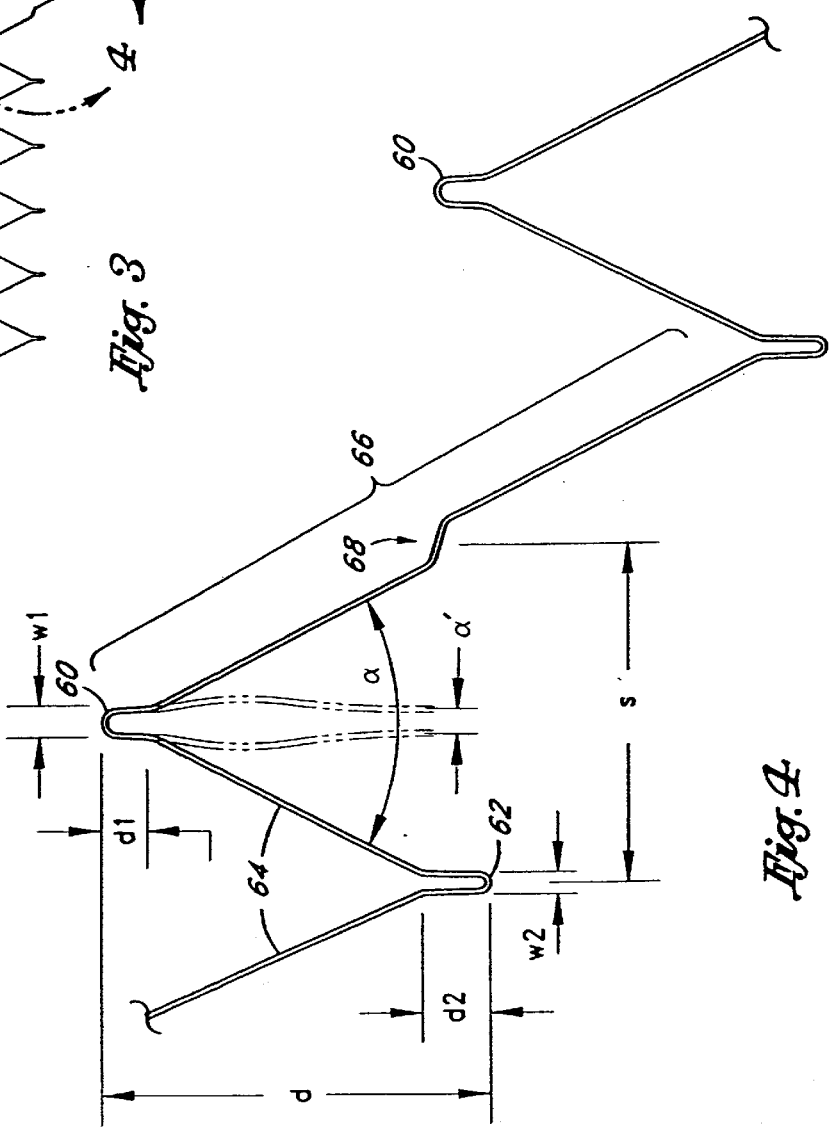
Fig. 3
Fig. 4

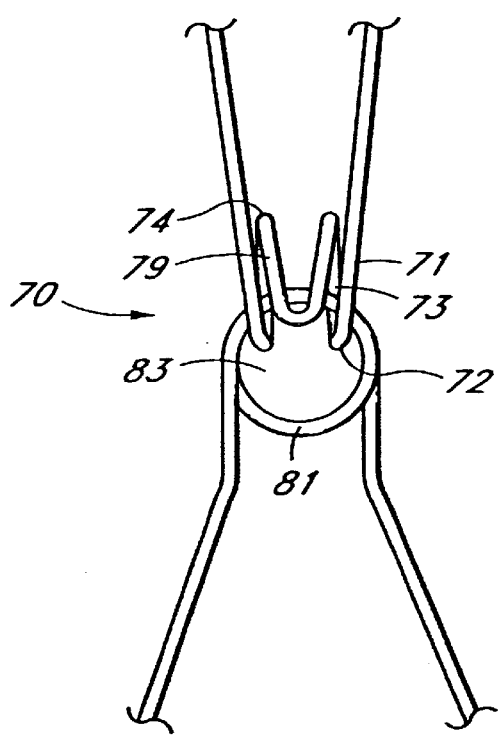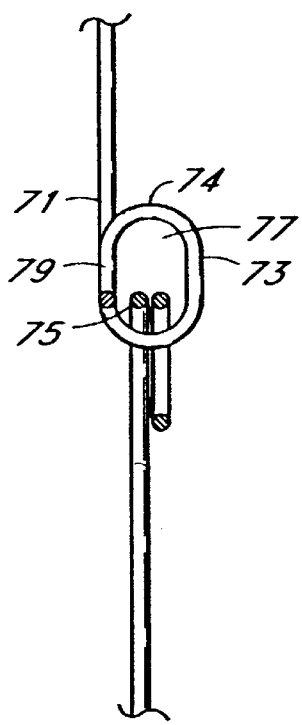

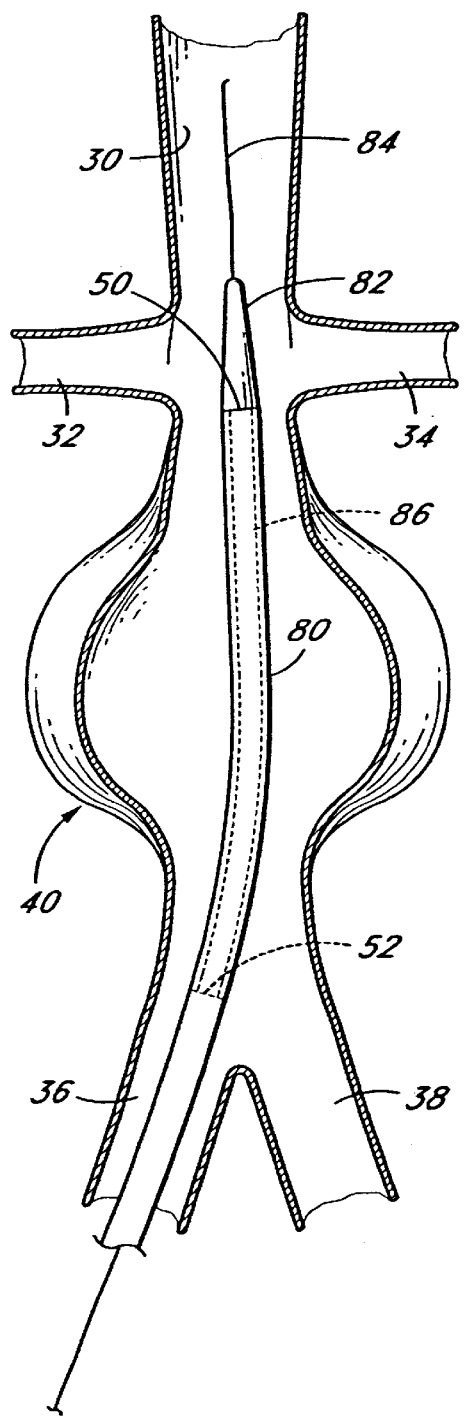
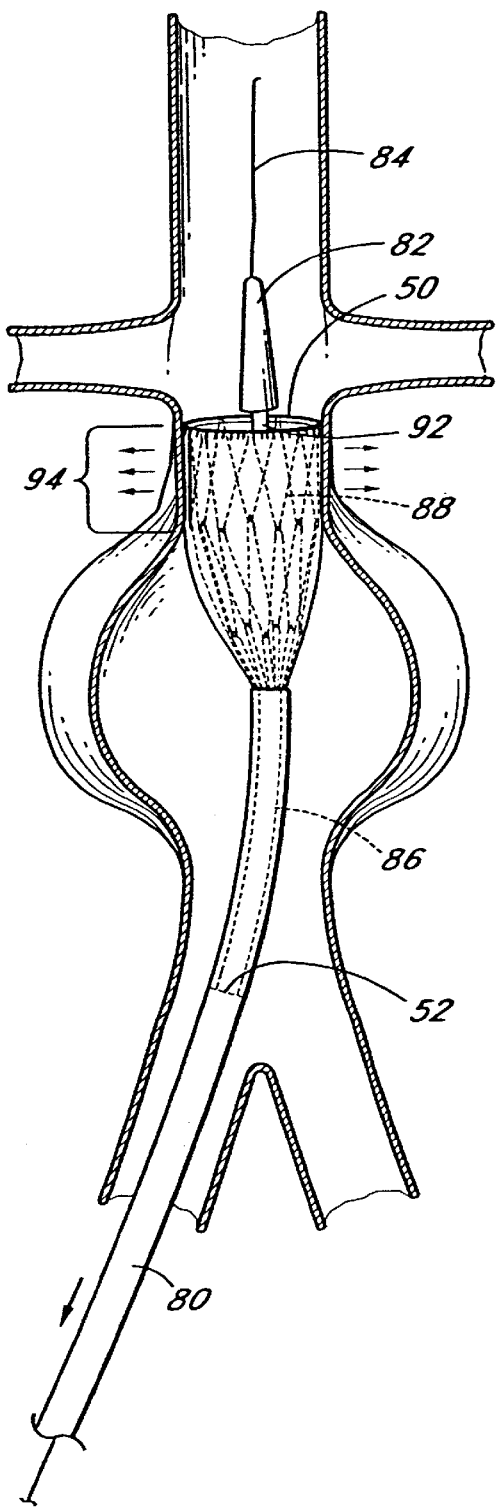
Fig. 13
Fig. 14

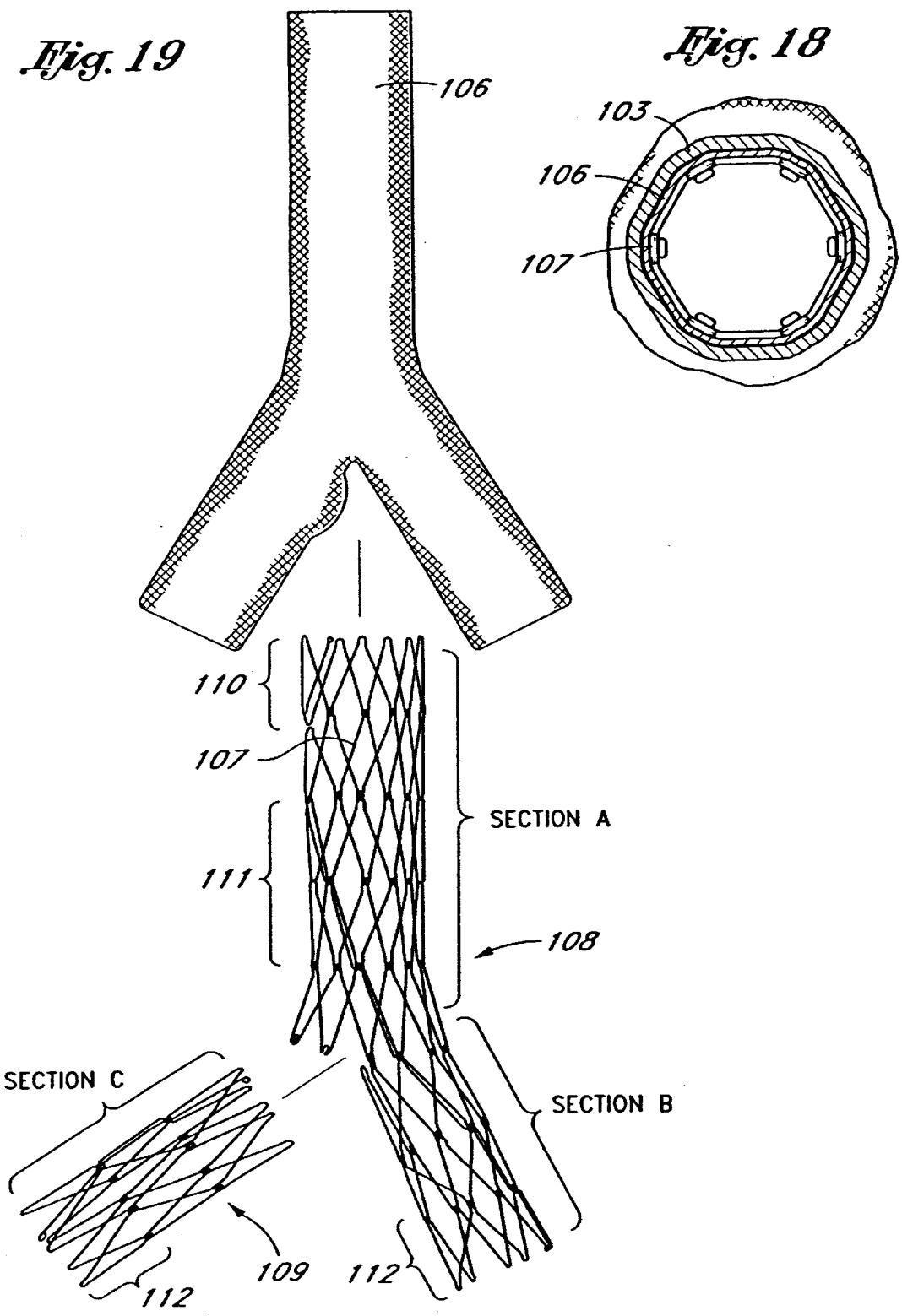

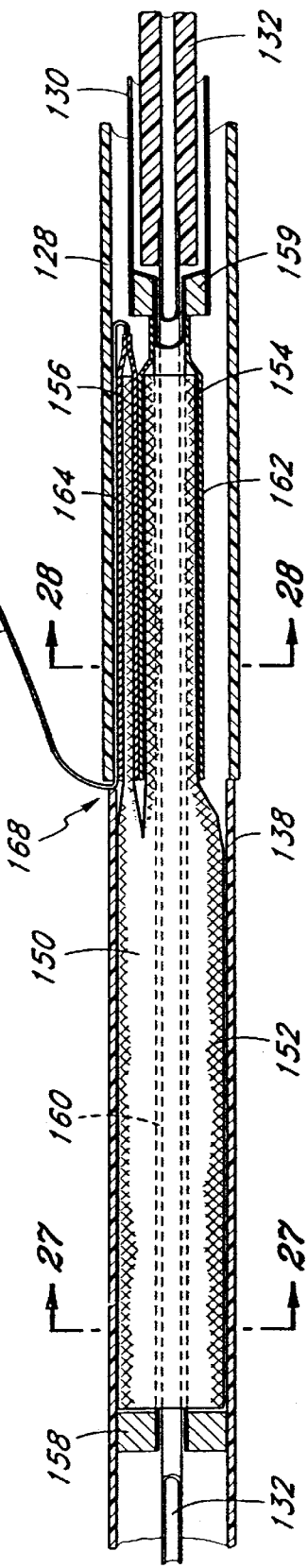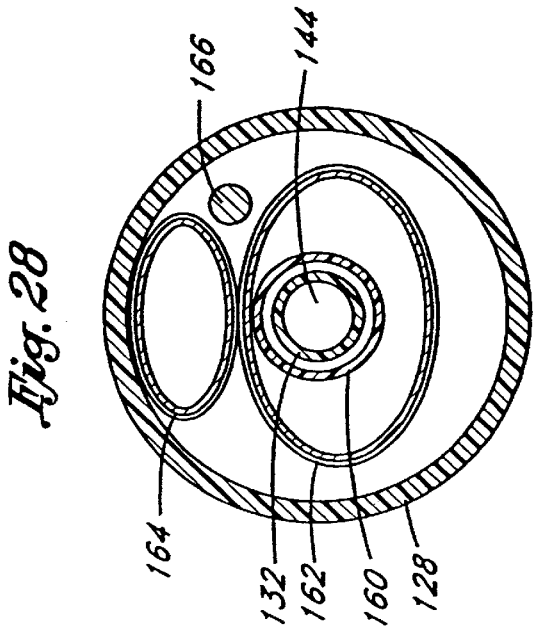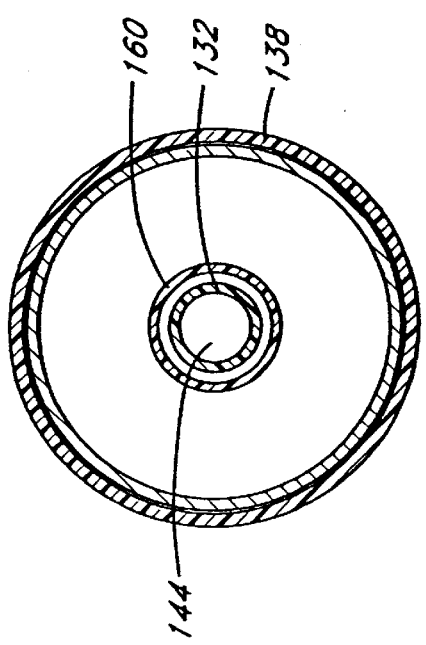

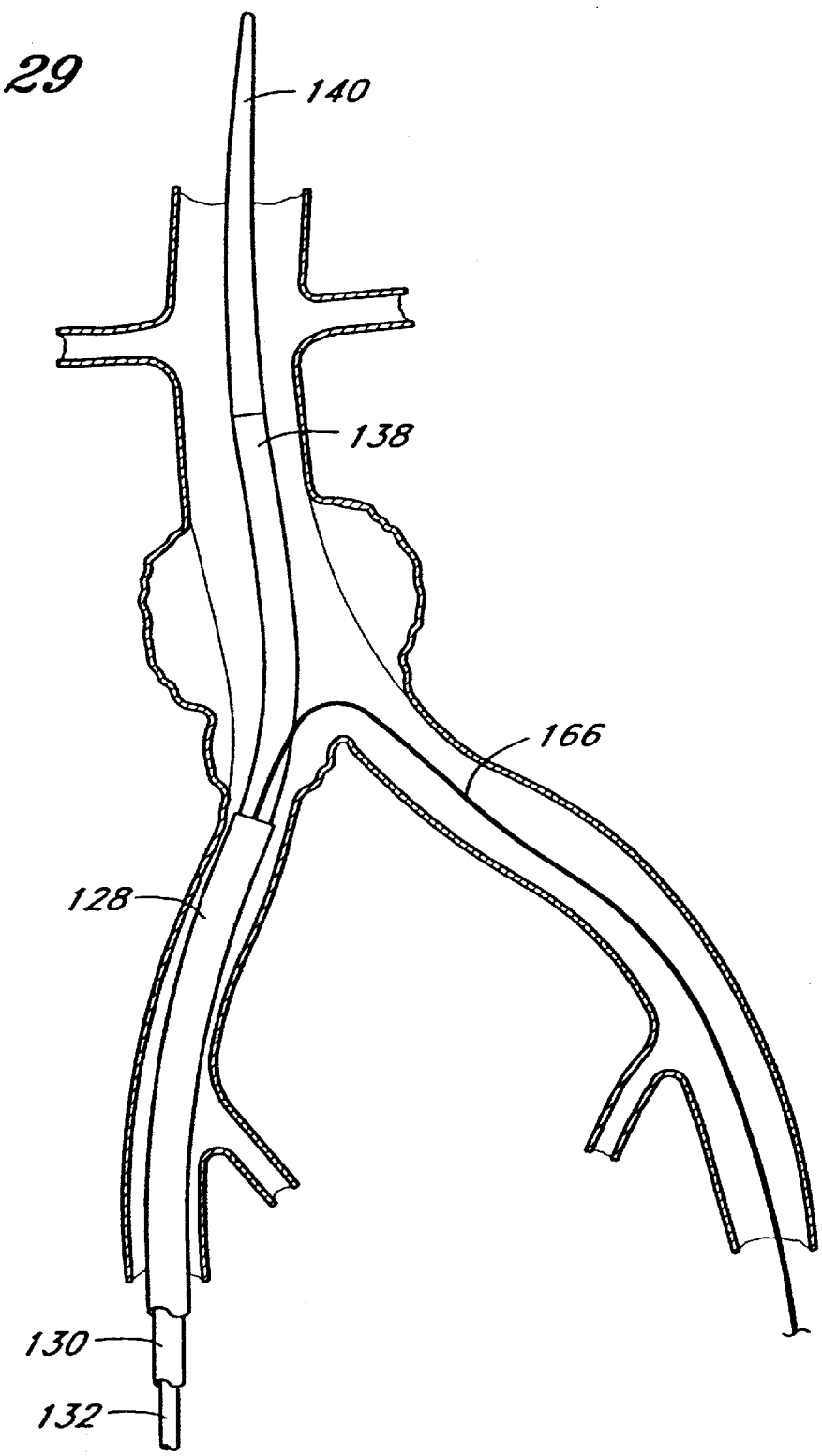

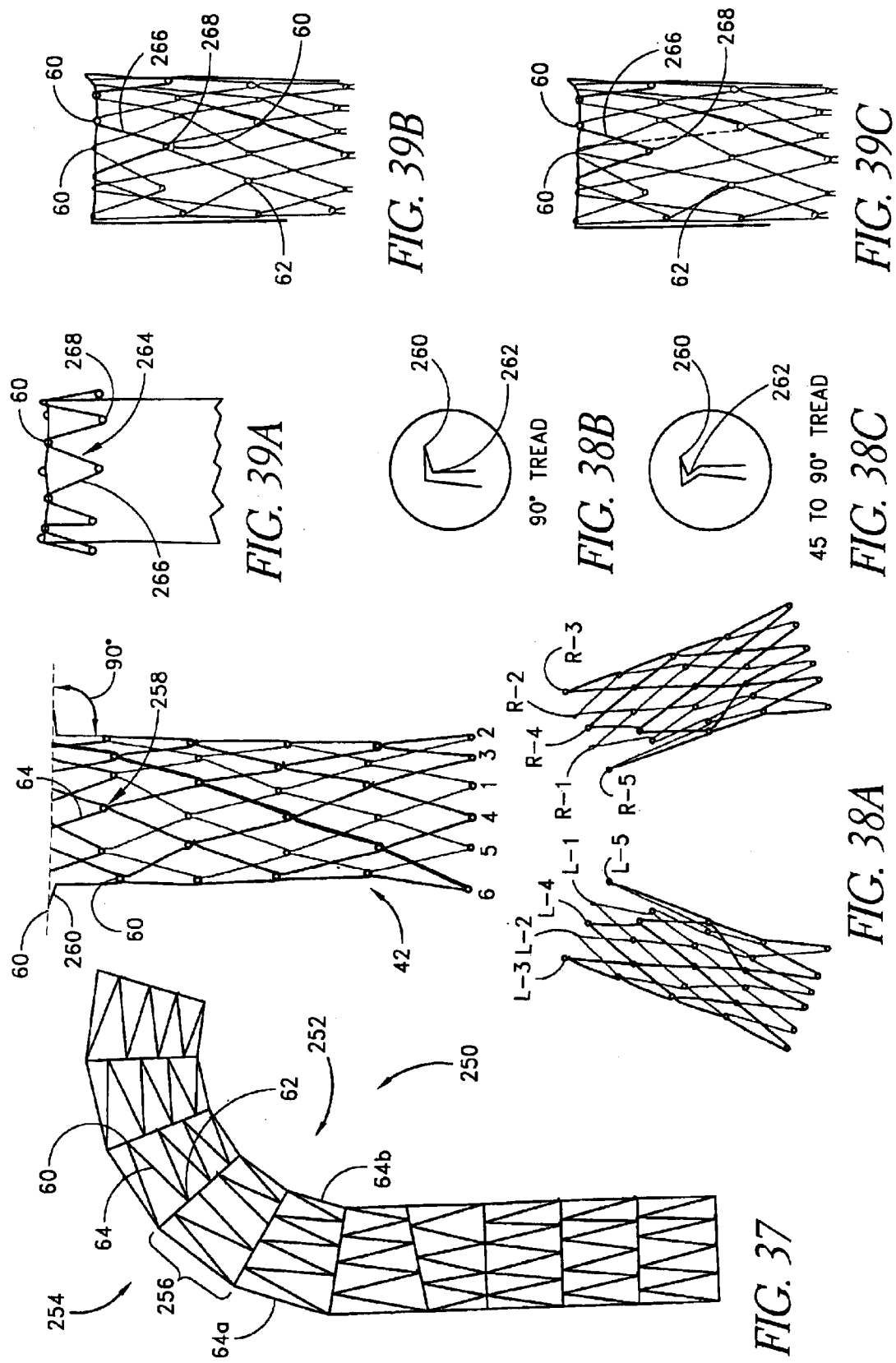

IMPLANTABLE VASCULAR GRAFT

This is a continuation-in-part of U.S. patent application Ser. No. 09/728,582, filed Dec. 1, 2000, which is a continuation-in-part of U.S. patent application Ser. No. 09/251,363, filed Feb. 17, 1999, entitled "Articulated Bifurcation Graft", now U.S. Pat. No. 6,197,049 which is a continuation-in-part of U.S. patent application Ser. No. 09/210,280, filed Dec. 11, 1998, entitled "Endoluminal Vascular Prosthesis", now U.S. Pat. No. 6,187,036.

BACKGROUND OF THE INVENTION

The present invention relates to an endoluminal vascular prosthesis, and in particular, to a self-expanding bifurcated prosthesis for use in the treatment of abdominal aortic aneurysms.

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON®, TEFLON®, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON® tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. The graft must be secured, or sutured, to the remaining portion of the aorta, which may be difficult to perform because of the thrombosis present on the remaining portion of the aorta. Moreover, the remaining portion of the aorta wall is frequently friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft within the lumen of the artery.

In general, transluminally implantable prostheses adapted for use in the abdominal aorta comprise a tubular wire cage surrounded by a tubular PTFE or Dacron sleeve. Both balloon expandable and self expandable support structures have been proposed. Endovascular grafts adapted to treat both straight segment and bifurcation aneurysms have also been proposed.

Notwithstanding the foregoing, there remains a need for a structurally simple, easily deployable transluminally implantable endovascular prosthesis, with a support structure adaptable to span either a straight or bifurcated aortic aneurysm. Preferably, the tubular prosthesis can be self expanded at the site to treat the abdominal aortic aneurysm, and exhibits flexibility to accommodate nonlinear anatomies and normal anatomical movement.

SUMMARY OF THE INVENTION

There is provided in accordance with one aspect of the present invention, an endoluminal prosthesis having an endoskeleton for supporting tubular polymeric sleeve, and a partial exoskeleton for positioning at the anatomically proximal end, to minimize migration and risks of endoleaks. The prosthesis comprises at least one elongate flexible wire, formed into a plurality of axially adjacent tubular segments spaced along an axis. Each tubular segment comprises a zig-zag section of wire, having a plurality of proximal bends and distal bends. At least one of the plurality of proximal bends and plurality of distal bends have loops thereon. A tubular polymeric sleeve is carried by the prosthesis.

The prosthesis is radially compressible into a first, reduced cross sectional configuration for implantation into a body lumen, and self expandable to a second, enlarged cross sectional configuration at a treatment site in a body lumen. At least a first portion of wire in one tubular segment is positioned on a radially outwardly facing surface of the sleeve. A radially inwardly facing surface of the sleeve is in contact with a second portion of wire.

In one application, the prosthesis comprises at least six proximal bends on a distal segment, and at least three of the proximal bends reside on the outside of the tubular sleeve and the remainder of the proximal bends are positioned on the inside of the tubular sleeve. At least about 30%, and generally from about 40% to about 70% of the proximal bends on a distal segment reside on the outside of the tubular sleeve. In this context, distal refers to catheter distal which is the same as anatomically proximal. The proximal bends on the inside of the tubular sleeve are connected to distal bends on a proximally adjacent segment inside of the tubular sleeve.

In accordance with another aspect of the present invention, there is provided a tubular wire support for a bifurcated endoluminal prosthesis. The wire support comprises a main body support structure having a proximal end, a distal end and a central lumen extending along a longitudinal axis therethrough. A first branch support structure, having a proximal end, a distal end and a central lumen therethrough, is provided such that the distal end of the first branch structure is connected to the proximal end of the main body support structure. A second branch support structure, having a proximal end, a distal end and a central lumen extending therethrough is provided, such that the distal end of the second branch support structure is connected to the proximal end of the main body support structure. A plurality of radially outwardly extending barbs or treads are provided on the main body, integrally formed on the wire support. The main body support structure and first and second branch support structures are preferably self expandable from a radially collapsed state to a radially expanded state.

The wire in each support structure is formed into a plurality of segments, each segment comprising a series of proximal bends, a series of distal bends, and a series of struts connecting the proximal and distal bends. The barbs may be formed by bending at least one of the proximal or distal bends such that it inclines radially outwardly from the longitudinal axis of the corresponding support structure. Preferably, the anchors comprise a plurality of distal bends on the main body support structure, to provide anchoring at the anatomically proximal end of the implanted tubular wire support.

In accordance with further aspect of the present invention, there is provided a tubular wire support for combination with a sheath to produce a flexible bifurcated endoluminal prosthesis. The wire support comprises a main body support structure having a proximal end, a distal end and a central lumen extending therethrough, the support structure comprising at least a first and second axially adjacent tubular segments. Each segment comprises a plurality of wall struts connected by proximal and distal bends.

A first branch support structure, having a proximal end, a distal end and a central lumen therethrough is connected to the main body support structure. A second branch support structure, having a proximal end, a distal end and a central lumen extending therethrough, is connected to the main body support structure. At least two sliding links are provided in between the first and second segments on the main body support structure and at least one lock is provided on a wall strut for limiting axial movement of a sliding link along that strut.

In one application, the lock comprises a loop formed into the strut, for limiting the effective length of travel of the sliding link along that strut. At least about 30%, and in some devices at least 50%, and in other devices 100% of the links in between the first and second segments are provided with a sliding link configuration. At least about 30%, and in some applications at least about 50% of the sliding links are provided with a lock on the corresponding strut.

In accordance with a further aspect of the present invention, there is provided a flexible self expandable graft. The graft comprises a tubular main body support structure, having a proximal end and a distal end. The tubular body comprises at least a first tubular segment attached to a second tubular segment. A tubular polymeric sleeve surrounds at least a portion of the graft. Each of the first and second tubular segments comprise a plurality of proximal bends and distal bends connected by struts, surrounding a longitudinal axis such that a first strut is on a first side of the axis and a second strut is on a second side of the axis opposing the first side. In at least one segment, the first strut is shorter than the second strut. In some applications, at least two or three or four or more adjacent segments are provided with a shorter strut or struts on a first side of the axis compared to the corresponding strut or struts on the second side of the axis, to facilitate curvature of the graft.

Further features and advantages of the present invention will become apparent to those of ordinary skill in the art in view of the disclosure herein, when considered together with the attached drawings and claims.

BRIEF DESCRIPTION OF THE DRAWINGS

FIG. 1 is a schematic representation of a straight segment vascular prosthesis in accordance with the present invention, positioned within a symmetric abdominal aortic aneurysm.

FIG. 2 is an exploded view of an endoluminal vascular prosthesis in accordance with the present invention, showing a self expandable wire support structure separated from an outer tubular sleeve.

FIG. 3 is a plan view of a formed wire useful for rolling about an axis into a multi-segment support structure in accordance with the present invention.

FIG. 4 is an enlarged detail view of a portion of the formed wire illustrated in FIG. 3.

FIGS. 6A, 7A, 8A, 7B, 8B, 7C, and 7D illustrate alternate embodiments of a folded link constructed from an opposing apex pair.

FIG. 13 is a schematic illustration of a straight segment delivery catheter in accordance with the present invention, positioned within an abdominal aortic aneurysm.

FIG. 14 is an illustration as in FIG. 13, with the straight segment endoluminal prosthesis partially deployed from the delivery catheter.

FIG. 18 is a cross-sectional view of the implanted graft taken along the lines 18—18 of FIG. 17.

FIG. 19 is an exploded view of the bifurcated vascular prosthesis in accordance with the present invention, showing a two-part self expandable wire support structure separated from an outer tubular sleeve.

FIG. 26 is an enlargement of the portion delineated by the line 26—26 in FIG. 25.

FIG. 27 is a cross-section taken along the line 27—27 in FIG. 26.

FIG. 28 is a cross-section taken along the line 28—28 in FIG. 26.

FIG. 29 is a schematic representation of a bifurcated graft deployment catheter of the present invention, positioned within the ipsilateral iliac and the aorta, with the contralateral guidewire positioned within the contralateral iliac.

FIG. 34b is a detail view of a sliding link in the embodiment of FIG. 34a.

FIG. 35b is a detail view of a sliding link in a proximal portion of the graft of FIG. 35a.

FIG. 35c is a detail view of a folded link utilized in an intermediate zone of the graft of FIG. 35a.

FIG. 35d is a detail view of a sliding link utilized in the iliac branches of the graft of FIG. 35a.

FIG. 37 is a schematic side elevational view of a graft having short graft sections on one side to facilitate a curve.

FIG. 38a illustrates a bifurcation or straight segment graft having a plurality of proximal barbs.

FIG. 38b is a detailed view of a barb of the type illustrated in FIG. 38a.

FIG. 38c is an alternate barb configuration.

FIG. 39a is a fractional side elevational view of a graft assembly having a partial exoskeleton.

FIG. 39b is a partial side elevational view of an alternate exoskeleton configuration.

FIG. 39c is a partial side elevational view of a second alternate partial exoskeleton configuration.

DETAILED DESCRIPTION OF THE PREFERRED EMBODIMENT

Figure 5:
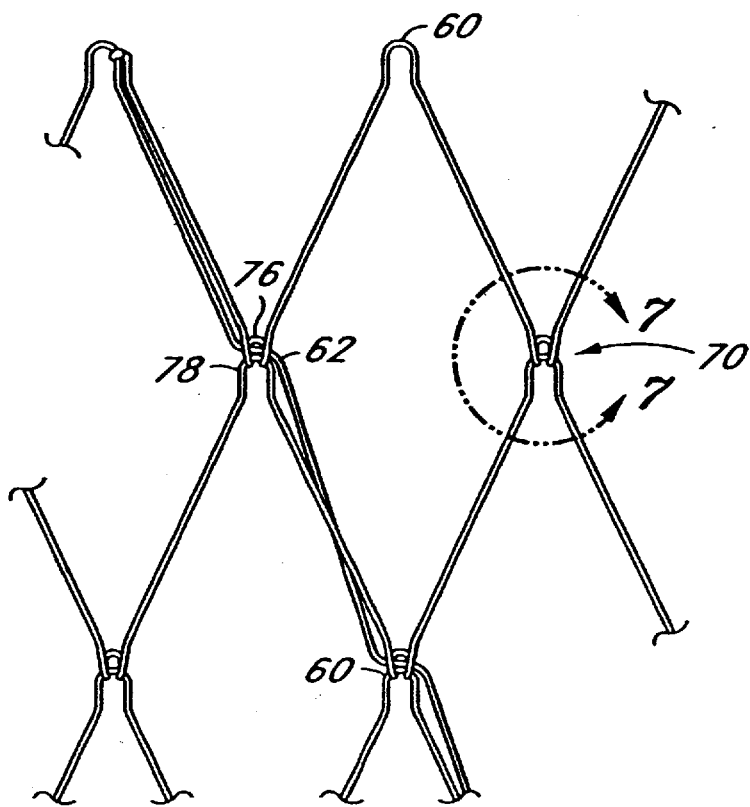
FIG. 5 is a schematic view of a portion of a wire cage wall, illustrating folded link connections between adjacent apexes.

Referring to FIG. 1, there is disclosed a schematic representation of the abdominal part of the aorta and its principal branches. In particular, the abdominal aorta 30 is characterized by a right renal artery 32 and left renal artery 34. The large terminal branches of the aorta are the right and left common iliac arteries 36 and 38. Additional vessels (e.g., second lumbar, testicular, inferior mesenteric, middle sacral) have been omitted for simplification. A generally symmetrical aneurysm 40 is illustrated in the infrarenal portion of the diseased aorta. An expanded straight segment endoluminal vascular prosthesis 42, in accordance with the present invention, is illustrated spanning the aneurysm 40.

The endoluminal vascular prosthesis 42 includes a polymeric sleeve 44 and a tubular wire support 46, which are illustrated in situ in FIG. 1. The sleeve 44 and wire support 46 are more readily visualized in the exploded view shown in FIG. 2. The endoluminal prosthesis 42 illustrated and described herein depicts an embodiment in which the polymeric sleeve 44 is situated concentrically outside of the tubular wire support 46. However, other embodiments may include a sleeve situated instead concentrically inside the wire support or on both of the inside and the outside of the wire support. Alternatively, the wire support may be embedded within a polymeric matrix which makes up the sleeve. Regardless of whether the sleeve 44 is inside or outside the wire support 46, the sleeve may be attached to the wire support by any of a variety of means, including laser bonding, adhesives, clips, sutures, dipping or spraying or others, depending upon the composition of the sleeve 44 and overall graft design.

The polymeric sleeve 44 may be formed from any of a variety of synthetic polymeric materials, or combinations thereof, including PTFE, PE, PET, Urethane, Dacron, nylon, polyester or woven textiles. Preferably, the sleeve material exhibits relatively low inherent elasticity, or low elasticity out to the intended enlarged diameter of the wire cage 46. The sleeve material preferably has a thin profile, such as no larger than about 0.002 inches to about 0.005 inches.

In a preferred embodiment of the invention, the material of sleeve 44 is sufficiently porous to permit ingrowth of endothelial cells, thereby providing more secure anchorage of the prosthesis and potentially reducing flow resistance, sheer forces, and leakage of blood around the prosthesis. Porosity in polymeric sleeve materials may be estimated by measuring water permeability as a function of hydrostatic pressure, which will preferably range from about 3 to 6 psi.

The porosity characteristics of the polymeric sleeve 44 may be either homogeneous throughout the axial length of the prosthesis 42, or may vary according to the axial position along the prosthesis 42. For example, referring to FIGS. 1 and 2, different physical properties will be called upon at different axial positions along the prosthesis 42 in use. At least a proximal portion 55 and a distal portion 59 of the prosthesis 42 will seat against the native vessel wall, proximally and distally of the aneurysm. In these proximal and distal portions, the prosthesis preferably encourages endothelial growth, or, at least, permits endothelial growth to infiltrate portions of the prosthesis in order to enhance anchoring and minimize leakage. A central portion 57 of the prosthesis spans the aneurysm, and anchoring is less of an issue. Instead, maximizing lumen diameter and minimizing blood flow through the prosthesis wall become primary objectives. Thus, in a central zone 57 of the prosthesis 42, the polymeric sleeve 44 may either be nonporous, or provided with pores of relatively lower porosity A multi-zoned prosthesis 42 may also be provided in accordance with the present invention by positioning a tubular sleeve 44 on a central portion 57 of the prosthesis, such that it spans the aneurysm to be treated, but leaving a proximal attachment zone 55 and a distal attachment zone 59 of the prosthesis 42 having exposed wires from the wire support 46. In this embodiment, the exposed wires 46 are positioned in contact with the vessel wall both proximally and distally of the aneurysm, such that the wire, over time, may become embedded in cell growth on the interior surface of the vessel wall.

In one embodiment of the prosthesis 42, the sleeve 44 and/or the wire support 46 is tapered, having a relatively larger expanded diameter at the proximal end 50 compared to the distal end 52. See, e.g., FIG. 36, discussed below. The tapered design may allow the prosthesis to conform better to the natural decreasing distal cross-section of the vessel, to reduce the risk of graft migration and potentially create better flow dynamics. The cage 46 can be provided with a proximal zone 55 and distal zone 59 that have a larger average expanded diameter than the central zone 57, as illustrated in FIG. 2. This configuration may desirably resist migration of the prosthesis within the vessel and reduce leakage around the ends of the prosthesis.

The tubular wire support 46 may be formed from a continuous single length of round or flattened wire. Alternatively, two or more wire lengths can be secured together to produce the wire support 46. The wire support 46 is preferably formed in a plurality of discrete tubular segments 54, connected together and oriented about a common axis. Each pair of adjacent segments 54 is connected by a connector 66 as illustrated in FIG. 3. The connectors 66 collectively produce a generally axially extending backbone which adds axial strength to the prosthesis 42. Adjacent segments can be connected both by the backbone, as well as the interlocking junction disclosed below. Additional structures, including circumferentially extending sutures, solder joints, and wire loops may also be used.

The segmented configuration of the tubular wire support 46 facilitates a great deal of flexibility. Each segment 54, though joined to adjacent segments, may be independently engineered to yield desired parameters. Each segment may range in axial length from about 0.3 to about 5 cm, and may be a uniform or non-uniform length around its circumference, such as to facilitate curvature as is discussed below. Generally, the shorter their length the greater the radial strength. An endoluminal prosthesis may include from about 1 to about 50 segments, preferably from about 3 to about 10 segments. For example, while a short graft patch, in accordance with the invention, may comprise only 2 segments and span a total of 2 to 3 cm, a complete graft may comprise 4 or more segments and span the entire aortic aneurysm. In addition to the flexibility and other functional benefits available through employment of different length segments, further flexibility can be achieved through adjustments in the number, angle, or configuration of the wire bends associated with the tubular support. See, eg., FIGS. 34 and 35, discussed below.

In addition to having differing expanded diameters in different zones of the prosthesis 42, different zones can be provided with a different radial expansion force, such as ranging from about 0.2 lbs. to about 0.8 lbs. In one embodiment, the proximal zone 55 is provided with a greater radial force than the central zone 57 and/or distal zone 59. The greater radial force can be provided in any of a variety of manners discussed elsewhere herein, such as through the use of an additional one or two or three or more proximal bends 60, distal bends 62 and wall sections 64 compared to a reference segment 54 in the central zone 57 or distal zone 59. Alternatively, additional spring force can be achieved in the proximal zone 55 through the use of the same number of proximal bends 60 as in the rest of the prosthesis, but with a heavier gauge wire.

The wire may be made from any of a variety of different alloys, such as elgiloy, nitinol or MP35N, or other alloys which include nickel, titanium, tantalum, or stainless steel, high Co-Cr alloys or other temperature sensitive materials. For example, an alloy comprising Ni 15%, Co 40%, Cr 20%, Mo 7% and balance Fe may be used. The tensile strength of suitable wire is generally above about 300 Ksi and often between about 300 and about 340 Ksi for many embodiments. In one embodiment, a Chromium-Nickel- Molybdenum alloy such as that marketed under the name Conichrom (Fort Wayne Metals, Ind.) has a tensile strength ranging from 300 to 320 K psi, elongation of 3.5–4.0%. The wire may be treated with a plasma coating and be provided with or without additional coatings such as PTFE, Teflon, Perlyne and drugs.

In addition to segment length and bend configuration, discussed above, another determinant of radial strength is wire gauge. The radial strength, measured at 50% of the collapsed profile, preferably ranges from about 0.2 lb. to 0.8 lb., and generally from about 0.4 lb. to about 0.5 lb. or more. Preferred wire diameters in accordance with the present invention range from about 0.004 inches to about 0.020 inches. More preferably, the wire diameters range from about 0.006 inches to about 0.018 inches. In general, the greater the wire diameter, the greater the radial strength for a given wire layout. Thus, the wire gauge can be varied depending upon the application of the finished graft, in combination with/or separate from variation in other design parameters (such as the number of struts, or proximal bends 60 and distal bends 62 per segment), as will be discussed. A wire diameter of approximately 0.018 inches may be useful in a graft having four segments each having 2.5 cm length per segment, each segment having six struts intended for use in the aorta, while a smaller diameter such as 0.006 inches might be useful for a 0.5 cm segment graft having 5 struts per segment intended for the iliac artery. The length of cage 42 could be as long as about 28 cm.

In one embodiment of the present invention, the wire diameter is tapered from the proximal to distal ends. Alternatively, the wire diameter may be tapered incrementally or stepped down, or stepped up, depending on differing radial strength requirements along the length of the graft for each particular clinical application. In one embodiment, intended for the abdominal aortic artery, the wire has a cross-section of about 0.018 inches in the proximal zone 55 and the wire tapers down to a diameter of about 0.006 inches in the distal zone 59 of the graft 42. End point dimensions and rates of taper can be varied widely, within the spirit of the present invention, depending upon the desired clinical performance.

Referring to FIG. 3, there is illustrated a plan view of a single formed wire used for rolling about a longitudinal axis to produce a four segment straight tubular wire support. The formed wire exhibits distinct segments, each corresponding to an individual tubular segment 54 in the tubular support (see FIGS. 1 and 2).

Each segment has a repeating pattern of proximal bends 60 connected to corresponding distal bends 62 by wall sections 64 which extend in a generally zig-zag configuration when the segment 54 is radially expanded. Each segment 54 is connected to the adjacent segment 54 through a connector 66, except at the terminal ends of the graft. The connector 66 in the illustrated embodiment comprises two wall or strut sections 64 which connect a proximal bend 60 on a first segment 54 with a distal bend 62 on a second, adjacent segment 54. The connector 66 may additionally be provided with a connector bend 68, which may be used to impart increased radial strength to the graft and/or provide a tie site for a circumferentially extending suture.

Referring to FIG. 4, there is shown an enlarged view of the wire support illustrating a connector 66 portion between adjacent segments 54. In the embodiment shown in FIG. 4, a proximal bend 60 comprises about a 180 degree arc, having a radial diameter of (w) (Ranging from 0.070 to 0.009 inches), depending on wire diameter followed by a relatively short length of parallel wire spanning an axial distance of d1. The parallel wires thereafter diverge outwardly from one another and form the strut sections 64, or the proximal half of a connector 66. At the distal end of the strut sections 64, the wire forms a distal bend 62, preferably having identical characteristics as the proximal bend 60, except being concave in the opposite direction. The axial direction component of the distance between the apices of the corresponding proximal and distal bends 60, 62 on a given strut section 64 is referred to as (d) and represents the axial length of that segment. The total expanded angle defined by the bend 60 and the divergent strut sections 64 is represented by $\alpha$. Upon compression to a collapsed state, such as when the graft is within the deployment catheter, the angle $\alpha$ is reduced to $\alpha'$. In the expanded configuration, $\alpha$ is generally within the range of from about 35° to about 45° for a six apex section having an axial length of about 1.5 cm or 2 cm and a diameter of about 25 mm or 28 mm. The expanded circumferential distance between any two adjacent distal bends 62 (or proximal bends 60) is defined as (s).

In general, the diameter W of each proximal bend 60 or distal bend 62 is within the range of from about 0.009 inches to about 0.070 inches depending upon the wire diameter. Diameter W is preferably as small as possible for a given wire diameter and wire characteristics. As will be appreciated by those of skill in the art, as the distance W is reduced to approach two times the cross-section of the wire, the bend 60 or 62 will exceed the elastic limit of the wire, and radial strength of the finished segment will be lost. Determination of a minimum value for W, in the context of a particular wire diameter and wire material, can be readily determined through routine experimentation by those of skill in the art.

As will be appreciated from FIG. 3 and 4, the sum of the distances (s) in a plane transverse to the longitudinal axis of the finished graft will correspond to the circumference of the finished graft cage in that plane. For a given circumference, the number of proximal bends 60 or distal bends 62 is directly related to the distance (s) in the corresponding plane. Preferably, the finished graft in any single transverse plane will have from about 3 to about 10 (s) dimensions, preferably from about 4 to about 8 (s) dimensions and, more preferably, about 5 or 6 (s) dimensions for an aortic application. Each (s) dimension corresponds to the distance between any two adjacent bends 60—60 or 62—62 as will be apparent from the discussion herein. Each segment 54 can thus be visualized as a series of triangles extending circumferentially around the axis of the graft, defined by a proximal bend 60 and two distal bends 62 or the reverse.

In one embodiment of the type illustrated in FIG. 4, w is about 2.0 mm±1 mm for a 0.018 inch wire diameter. D1 is about 3 mm±1 mm, and d is about 20 mm±1 mm. Specific dimensions for all of the foregoing variables can be varied considerably, depending upon the desired wire configuration, in view of the disclosure herein.

Figure 6:
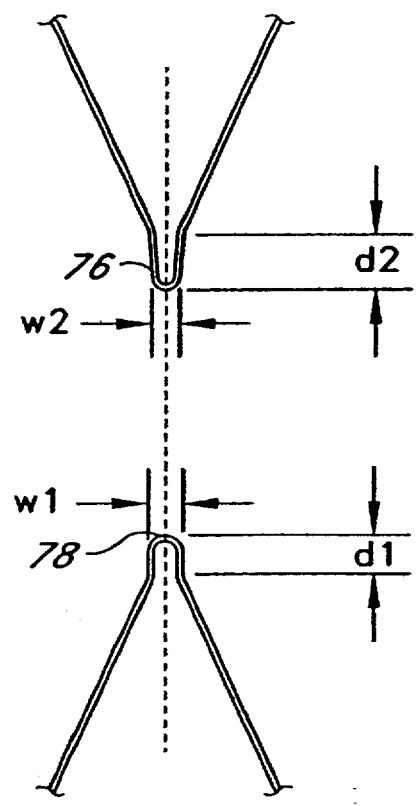
FIG. 6 is an exploded view of two opposing apexes dimensioned for one embodiment of the folded link connection of the present invention.

Referring to FIGS. 5 and 6, one or more apexes 76 is provided with an elongated axial length d2, which permits the apex 76 to be wrapped around a corresponding portion 78 such as an apex of the adjacent segment to provide an interlocking link 70 between two axially adjacent cage segments. In one embodiment of the link 70 produced by the opposing apexes 76 and 78 of FIG. 6, utilizing wire having a diameter from 0.012" to 0.018", d1 is generally within the range of from about 1 mm to about 4 mm and d2 is within the range of from about 5 mm to about 9 mm. In general, a longer d2 dimension permits accommodation for greater axial travel of apex 78 with respect to 76, as will be discussed, thereby permitting greater lateral flexibility of the graft. W1 is within the range of from about 3 mm to about 5 mm, and W2 is sufficiently less than W1 that the apex 76 can fit within the apex 78. Any of a wide variety of specific apex configurations and dimensions can be utilized, as will be apparent to those of skill in the art in view of the disclosure herein. Regardless of the specific dimensions, the end of the apex 76 is advanced through the apex 78, and folded back upon its self to hook the apex 78 therein to provide a link 70 in accordance with the present invention.

Figure 10:
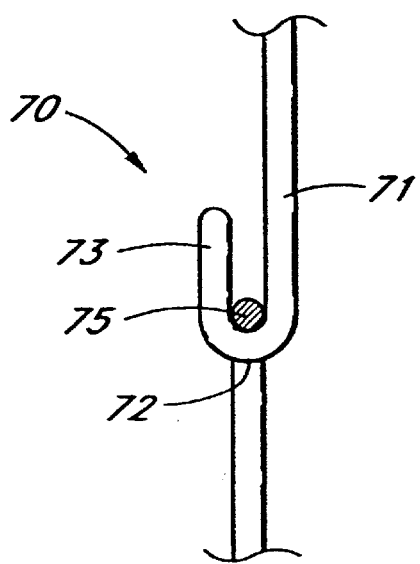
FIG. 10 is a cross-section taken along the line 10—10 in FIG. 9.
Figure 11:
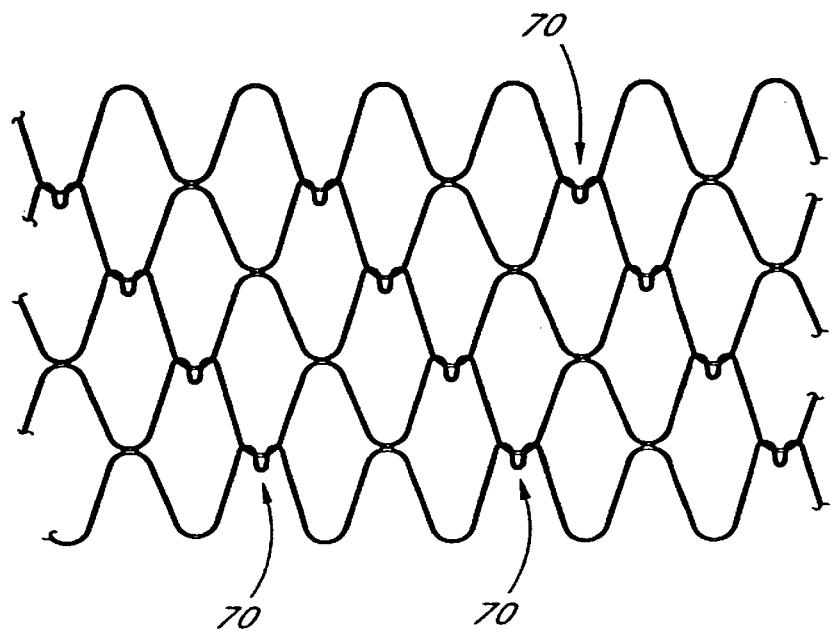
FIG. 11 is a schematic view of a portion of a wall of a graft, laid out flat, illustrating an alternating folded link pattern.

The resulting link 70 (see FIGS. 7 and 8) comprises a wall portion 71 extending in a first direction, substantially parallel to the axis of the graft, and a transverse portion 72 extending transverse to the axis of the graft. A return portion 73 extends generally in the opposite direction from the wall portion 71 to create a generally "U" shaped hook. In certain embodiments, a closing portion 74 is also provided, to minimize the risk of excessive axial compression of the wire cage. The forgoing structure produces a functionally closed aperture 77, which receives the interlocking section 75 of the adjacent graft segment. Alternatively, see FIG. 10.

In general, the aperture 77 preferably has a width (as viewed in FIG. 8) in the radial graft direction of substantially equal to the radial direction dimension of the interlocking section 75. In this embodiment, the interlocking section 75, as well as the locking portion 71 and return portion 73 can be flattened in the radial direction, to minimize the transverse cross-section of the link 70. In the axial direction, the aperture 77 is preferably greater than the axial direction dimension of the interlocking section 75, to accommodate some axial movement of each adjoining tubular segment of the graft. The axial length of the aperture 77 is at least about 2 times, and preferably at least about 3 or 4 times the cross-section of the interlocking section 75. The optimum axial length of the aperture 77 can be determined through routine experimentation by one of skill in the art in view of the intended clinical performance, taking into account the number of links 70 per transverse plane as well as the desired curvature of the finished graft.

Figure 6A:
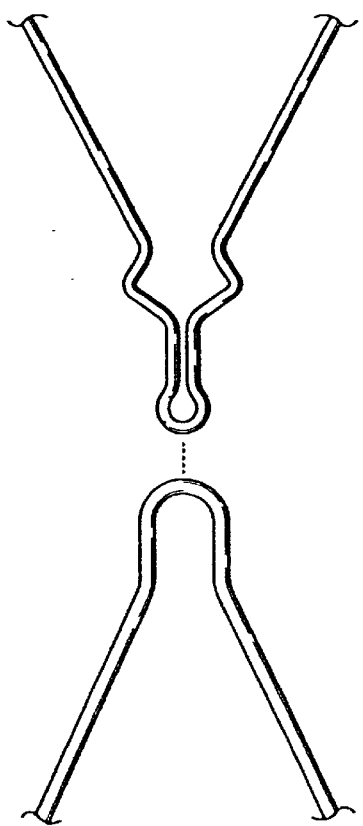
Figure 7A:
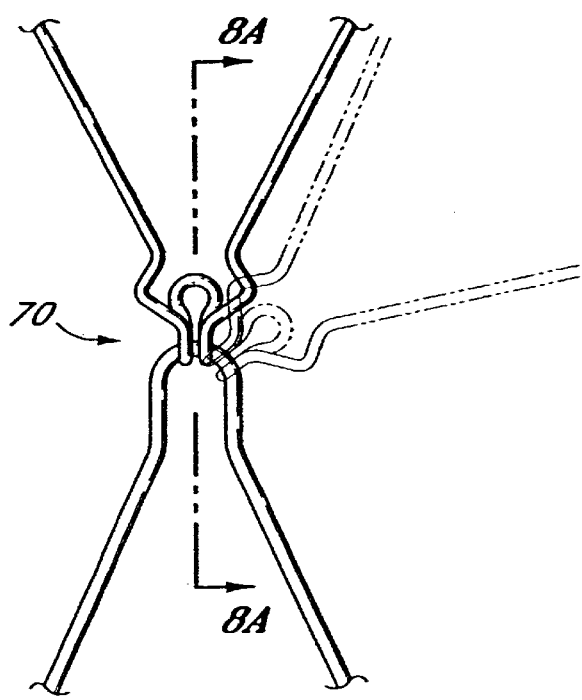
Figure 8A:
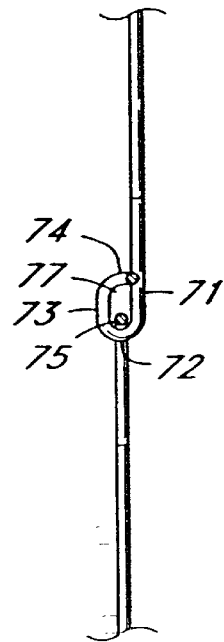
Figure 7:
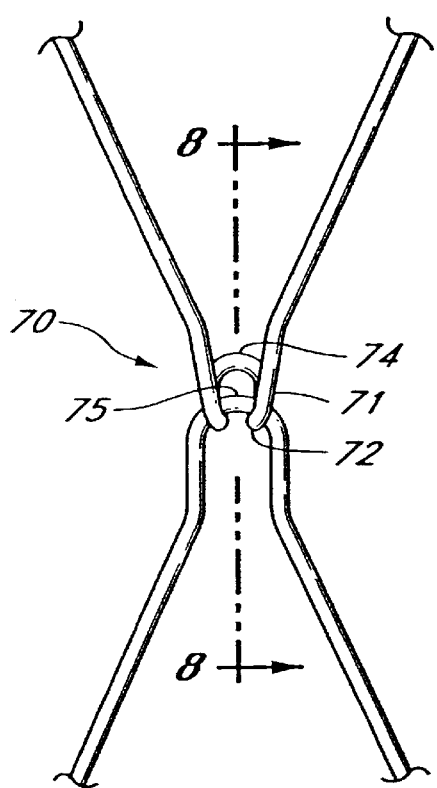
FIG. 7 is an enlarged view of a folded link, taken along the lines 7—7 in FIG. 5.
Figure 8:
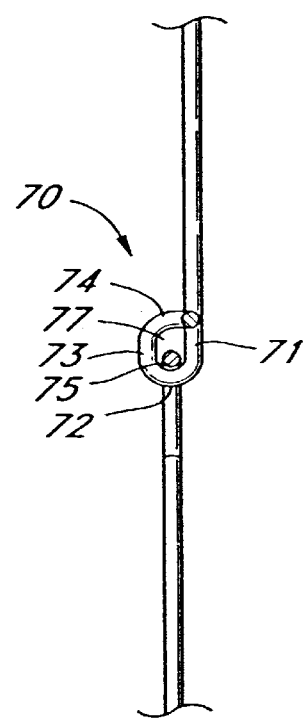
FIG. 8 is a cross-sectional view taken along the line 8—8 in FIG. 7.

FIGS. 6A, 7A and 8A illustrate an alternate configuration for the moveable link 70. With this configuration, the radial expansion force will be higher.

Figure 7C:
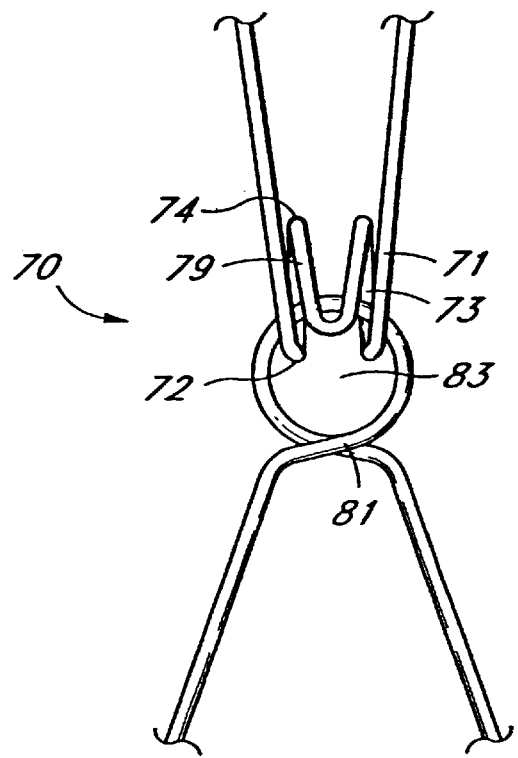
Figure 7D:
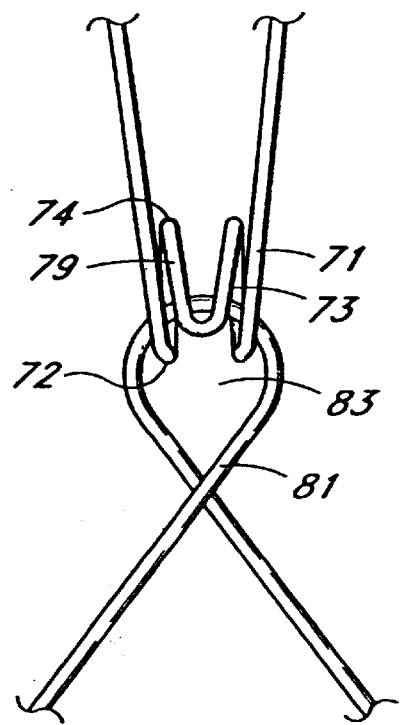

FIGS. 7B and 8B illustrate another alternate configuration. This linkage has a better resistance to axial compression and disengagement. Referring to FIGS. 7B and 8B, the apex extends beyond closing portion 74 and into an axial portion 79 which extends generally parallel to the longitudinal axis of the graft. Provision of an axial extension 79 provides a more secure enclosure for the aperture 77 as will be apparent to those of skill in the art. The embodiments of FIG. 7B and 8B also illustrate an enclosed aperture 83 on the opposing apex. The aperture 83 is formed by wrapping the apex in at least one complete revolution so that a generally circumferentially extending portion 81 is provided. Circumferential portion 81 provides a stop, to limit axial compressibility of the graft. The closed aperture 83 can be formed by winding the wire of the apex about a mandrel either in the direction illustrated in FIG. 7B, or the direction illustrated in FIG. 7C. The embodiment of FIG. 7C advantageously provided only a single wire thickness through the aperture 77, thereby minimizing the wall thickness of the graft. This is accomplished by moving the crossover point outside of the aperture 77, as will be apparent from FIG. 7C.

The link 70 in accordance with the present invention is preferably formed integrally with the wire which forms the cage of the endovascular prosthesis. Alternatively, link 70 may be constructed from a separate material which is secured to the wire cage such as by soldering, suture, wrapping or the like.

Figure 9:
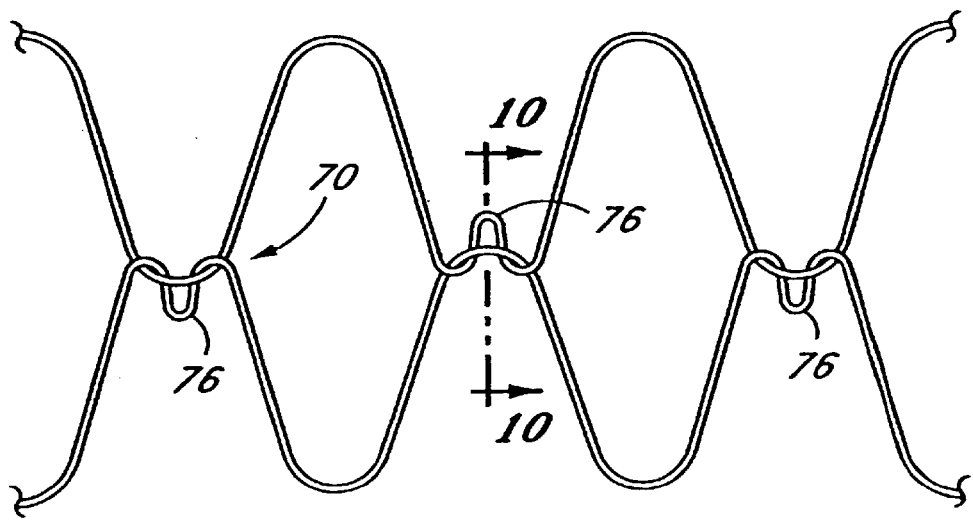
FIG. 9 is a partial view of a junction between two adjacent tubular segments, illustrating oppositely oriented folded links in accordance with the present invention.

The axial direction of the link 70 may also be varied, depending upon the desired performance characteristics of the graft. For example, the distal tips 76 of each link 70 may all face the same direction, such as proximal or distal with respect to the graft. See, for example, FIG. 5. Alternatively, one or more links in a given transverse plane of apexes may face in a proximal direction, and one or more links in the same transverse plane may face in the opposite direction. See, for example, FIG. 9.

Regardless of the axial orientation of the link 70, at least one and preferably at least two links 70 are provided per transverse plane separating adjacent graft segments. In an embodiment having six apexes per transverse plane, preferably at least two or three and in one embodiment all six opposing apex pairs are provided with a link 70. See FIG. 5.

The distribution of the interlocking link 70 throughout the wire cage can thus vary widely, depending upon the desired performance characteristics. For example, each opposing apex pair between adjacent tubular segments can be provided with a link 70. See FIG. 5. Alternatively, interlocking links 70 may be spaced circumferentially apart around the graft wall such as by positioning them at every second or third opposing apex pair.

Figure 12:
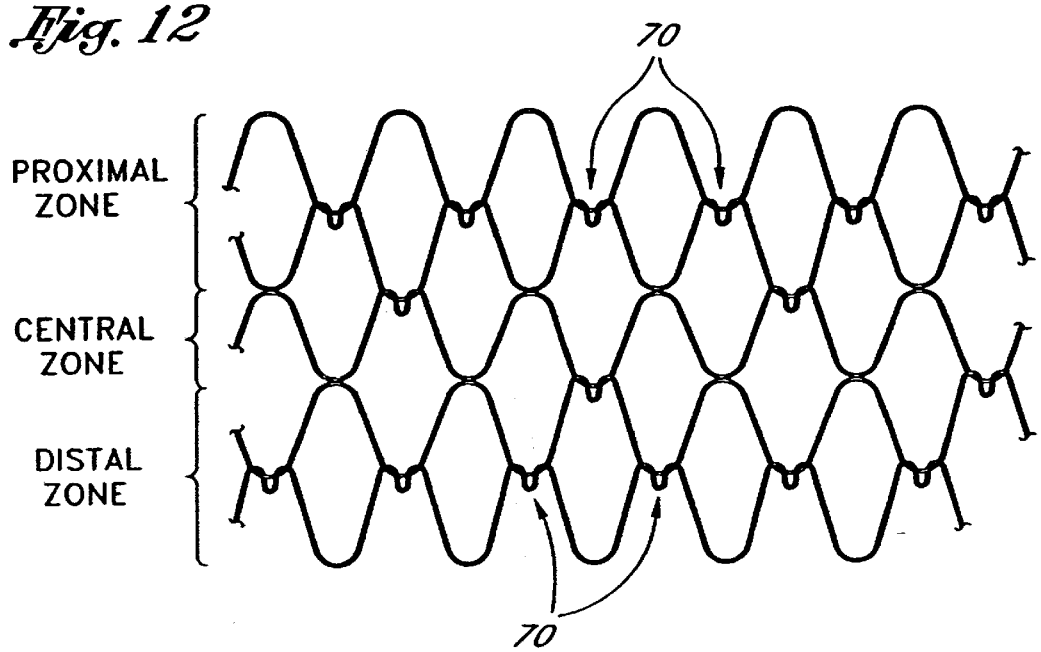
FIG. 12 is a wall pattern as in FIG. 11, illustrating a multi-zone folded link pattern.

The distribution of the links 70 may also be varied along the axial length of the graft. For example, a first zone at a proximal end of the graft and a second zone at a distal end of the graft may be provided with a relatively larger number of links 70 than a third zone in the central portion of the graft. In one embodiment, the transverse apex plane between the first and second tubular segments at the proximal end of the graft may be provided with a link 70 at each opposing apex pair. This has been determined by the present inventors to increase the radial strength of the graft, which may be desirable at the proximal (superior) end of the graft and possibly also at the distal end of the graft where resistance to leakage is an issue. A relatively lesser radial strength may be necessary in the central portion of the graft, where maintaining patency of the lumen is the primary concern. For this reason, relatively fewer links 70 may be utilized in a central zone, in an effort to simplify graft design as well as reduce collapse profile of the graft. See FIG. 12.

In one straight segment graft, having four graft segments, three transverse apex planes are provided. In the proximal apex plane, each opposing pair of apexes is provided with a link 70. In the central transverse apex plane, three of the six apex pairs are provided with a links 70, spaced apart at approximately 120°. Substantially equal circumferential spacing of the link 70 is preferred, to provide relatively uniform resistance to bending regardless of graft position. The distal transverse apex plane may also be provided with a link 70 at each opposing apex pair.

The foregoing interlocking link 70 in accordance with the present invention can be readily adapted to both the straight segment grafts as discussed above, as well as to the bifurcated grafts discussed below.

The interlocking link 70 can be utilized to connect any of a number of independent graft segments in axial alignment to produce either a straight segment or a bifurcation graft. The interlocking link 70 may be utilized as the sole means of securing adjacent segments to each other, or may be supplemented by additional attachment structures such as metal loops, sutures, welds and others which are well understood in the art.

Figure 12A:
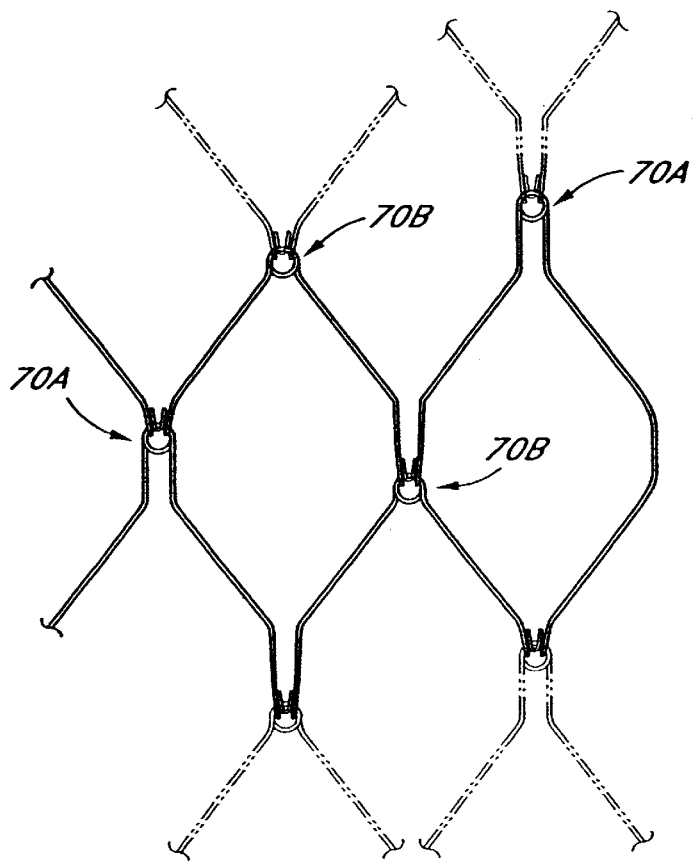
FIGS. 12A through 12C illustrate an alternate wall pattern, which permits axially staggered links between adjacent graft segments.
Figure 12B:
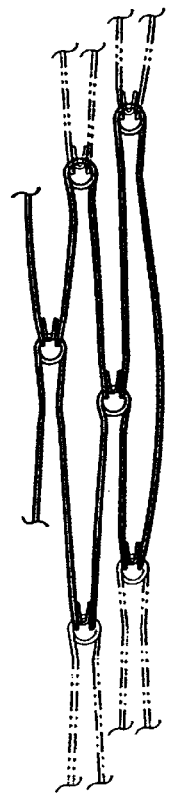
Figure 12C:
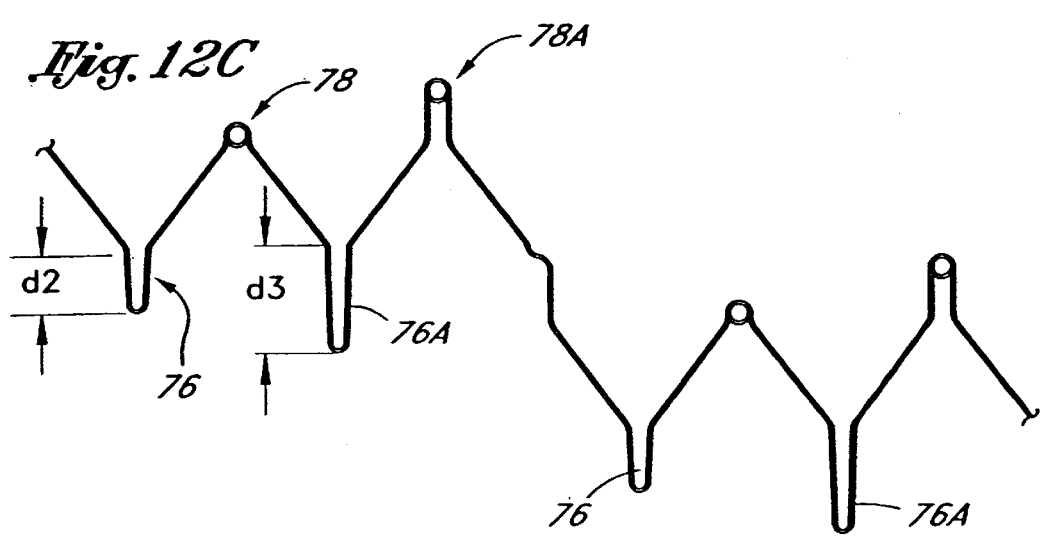

Referring to FIGS. 12A through 12C there is illustrated a further wire layout which allows a smaller collapsed profile for the vascular graft. In general, the embodiment of FIGS. 12A through 12C permits a series of links 70A and 70B to be staggered axially from one another as seen in FIG. 12A and 12B. In this manner, adjacent links 70 do not lie in the same transverse plane, and permit a tighter nesting of the collapsed wire cage. Preferably, between each adjoining graft segment, at least a first group of links 70A is offset axially from a second group of links 70B. In a six apex graft, having a link 70 at each apex, for example, a first group of every other apex 70A may be positioned slightly proximally of a second group of every other apex 70B. Referring to FIG. 12C, this may be accomplished by extending an apex 76A by a d3 distance which is at least about 1.2 times and as large as 1.5 times or 2 times or more the distance d2. The corresponding apexes 78 and 78A are similarly staggered axially, to produce the staggered interface between adjacent graft segments illustrated in FIG. 12A. Although a loop apex is illustrated in FIG. 12C as apex 78, any of the alternate apexes illustrated herein can be utilized in the staggered apex embodiment of the invention. The zig-zag pattern produced by axially offset links 70A and 70B can reside in a pair of parallel transverse planes extending generally between adjacent segments of the graft. Alternatively, the zig-zag relationship between adjacent links 70A and 70B can spiral around the circumference of a graft in a helical pattern, as will be understood by those of skill in the art in view of the disclosure herein. The precise axial offset between adjacent staggered links 70A and 70B can be optimized by one of ordinary skill in the art through routine experimentation, taking into account the desired physical properties and collapsed profile of the graft.

Referring to FIGS. 13 and 14, a straight segment deployment device and method in accordance with a preferred embodiment of the present invention are illustrated. A delivery catheter 80, having a dilator tip 82, is advanced along guidewire 84 until the (anatomically) proximal end 50 of the collapsed endoluminal vascular prosthesis 88 is positioned between the renal arteries 32 and 34 and the aneurysm 40. The collapsed prosthesis in accordance with the present invention has a diameter in the range of about 2 to about 10 mm. Generally, the diameter of the collapsed prosthesis is in the range of about 3 to 6 mm (12 to 18 French). Preferably, the delivery catheter including the prosthesis will be 16 F, or 15 F or 14 F or smaller.

The prosthesis 88 is maintained in its collapsed configuration by the restraining walls of the tubular delivery catheter 80, such that removal of this restraint would allow the prosthesis to self expand. Radiopaque marker material may be incorporated into the delivery catheter 80, and/or the prosthesis 88, at least at both the proximal and distal ends, to facilitate monitoring of prosthesis position. The dilator tip 82 is bonded to an internal catheter core 92, as illustrated in FIG. 14, so that the internal catheter core 92 and the partially expanded prosthesis 88 are revealed as the outer sheath of the delivery catheter 80 is retracted.

As the outer sheath is retracted, the collapsed prosthesis 88 remains substantially fixed axially relative to the internal catheter core 92 and consequently, self-expands at a predetermined vascular site as illustrated in FIG. 14. Continued retraction of the outer sheath results in complete deployment of the graft. After deployment, the expanded endoluminal vascular prosthesis 88 has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

In addition to, or in place of, the outer sheath described above, the prosthesis 88 may be maintained in its collapsed configuration by a restraining lace, which may be woven through the prosthesis or wrapped around the outside of the prosthesis in the collapsed reduced diameter. Following placement of the prosthesis at the treatment site, the lace can be proximally retracted from the prosthesis thereby releasing it to self expand at the treatment site. The lace may comprise any of a variety of materials, such as sutures, strips of PTFE, FEP, polyester fiber, and others as will be apparent to those of skill in the art in view of the disclosure herein. The restraining lace may extend proximally through a lumen in the delivery catheter or outside of the catheter to a proximal control. The control may be a pull tab or ring, rotatable reel, slider switch or other structure for permitting proximal retraction of the lace. The lace may extend continuously throughout the length of the catheter, or may be joined to another axially moveable element such as a pull wire.

In general, the expanded diameter of the graft in accordance with the present invention can be any diameter useful for the intended lumen or hollow organ in which the graft is to be deployed. For most arterial vascular applications, the expanded size will be within the range of from about 10 to about 40 mm. Abdominal aortic applications will generally require a graft having an expanded diameter within the range of from about 20 to about 28 mm, and, for example, a graft on the order of about 45 mm may be useful in the thoracic artery. The foregoing dimensions refer to the expanded size of the graft in an unconstrained configuration, such as on the table. In general, the graft will be positioned within an artery having a slightly smaller interior cross-section than the expanded size of the graft. This enables the graft to maintain a slight positive pressure against the wall of the artery, to assist in retention of the graft during the period of time prior to endothelialization of the polymeric sleeve 44.

The radial force exerted by the proximal segment 94 of the prosthesis against the walls of the aorta 30 provides a seal against the leakage of blood around the vascular prosthesis and tends to prevent axial migration of the deployed prosthesis. As discussed above, this radial force can be modified as required through manipulation of various design parameters, including the axial length of the segment and the bend configurations. In another embodiment of the present invention, radial tension can be enhanced at the proximal, upstream end by increasing the wire gauge in the proximal zone. Wire diameter may range from about 0.001 to 0.01 inches in the distal region to a range of from about 0.01 to 0.03 inches in the proximal region.

An alternative embodiment of the wire layout which would cause the radial tension to progressively decrease from the proximal segments to the distal segments, involves a progressive or step-wise decrease in the wire gauge throughout the entire wire support, from about 0.01 to 0.03 inches at the proximal end to about 0.002 to 0.01 inches at the distal end. Such an embodiment, may be used to create a tapered prosthesis. Alternatively, the wire gauge may be thicker at both the proximal and distal ends, in order to insure greater radial tension and thus, sealing capacity. Thus, for instance, the wire gauge in the proximal and distal segments may about 0.01 to 0.03 inches, whereas the intervening segments may be constructed of thinner wire, in the range of about 0.001 to 0.01 inches.

Figure 15:
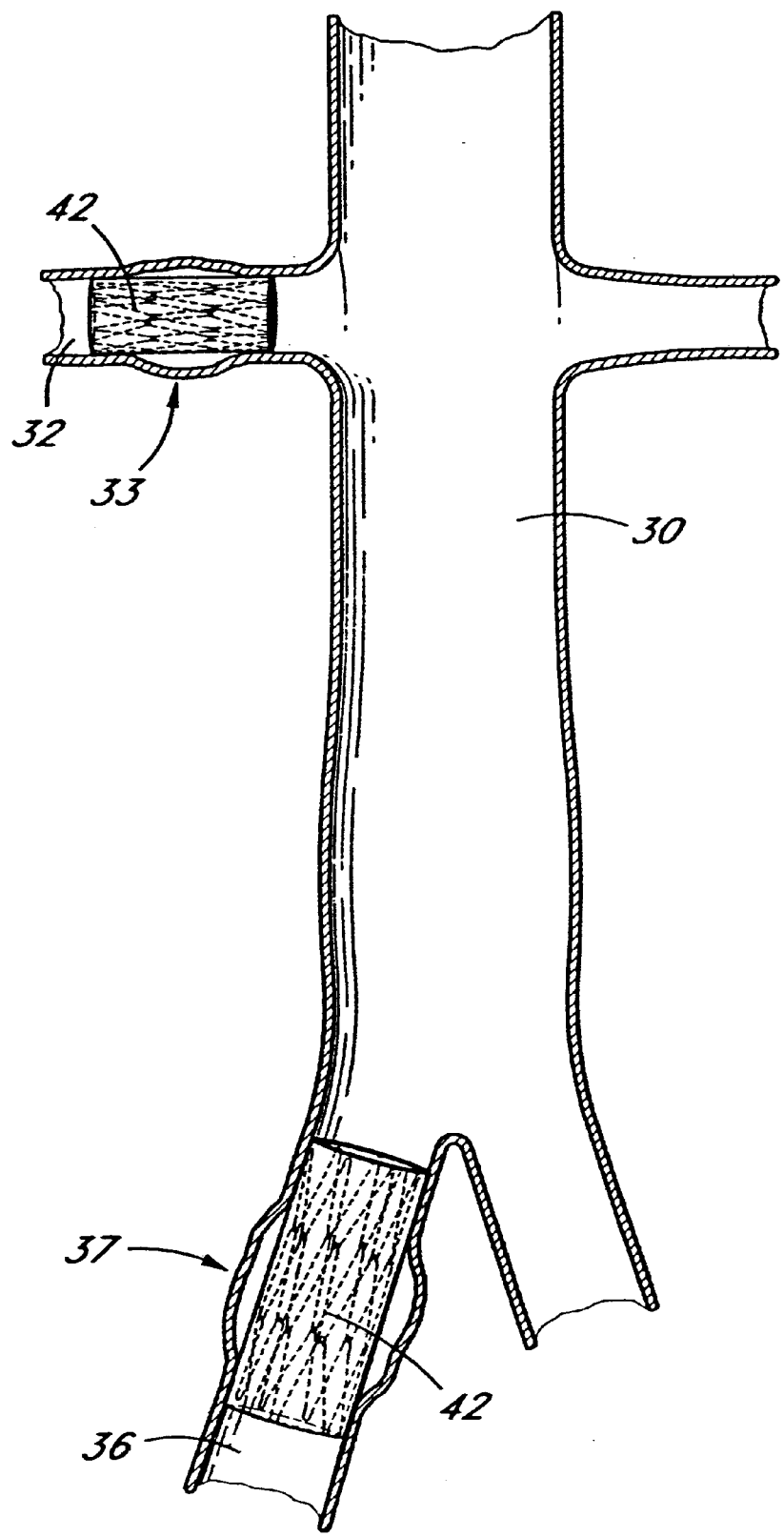
FIG. 15 is a schematic representation of the abdominal aortic anatomy, with an endoluminal vascular prostheses of the present invention positioned within each of the right renal artery and the right common iliac.

Referring to FIG. 15, there is illustrated two alternative deployment sites for the endoluminal vascular prosthesis 42 of the present invention. For example, an aneurysm 33 is illustrated in the right renal artery 32. An expanded endoluminal vascular prosthesis 42, in accordance with the present invention, is illustrated spanning that aneurysm 33. Similarly, an aneurysm 37 of the right common iliac 36 is shown, with a prosthesis 42 deployed to span the iliac aneurysm 37.

Figure 16:
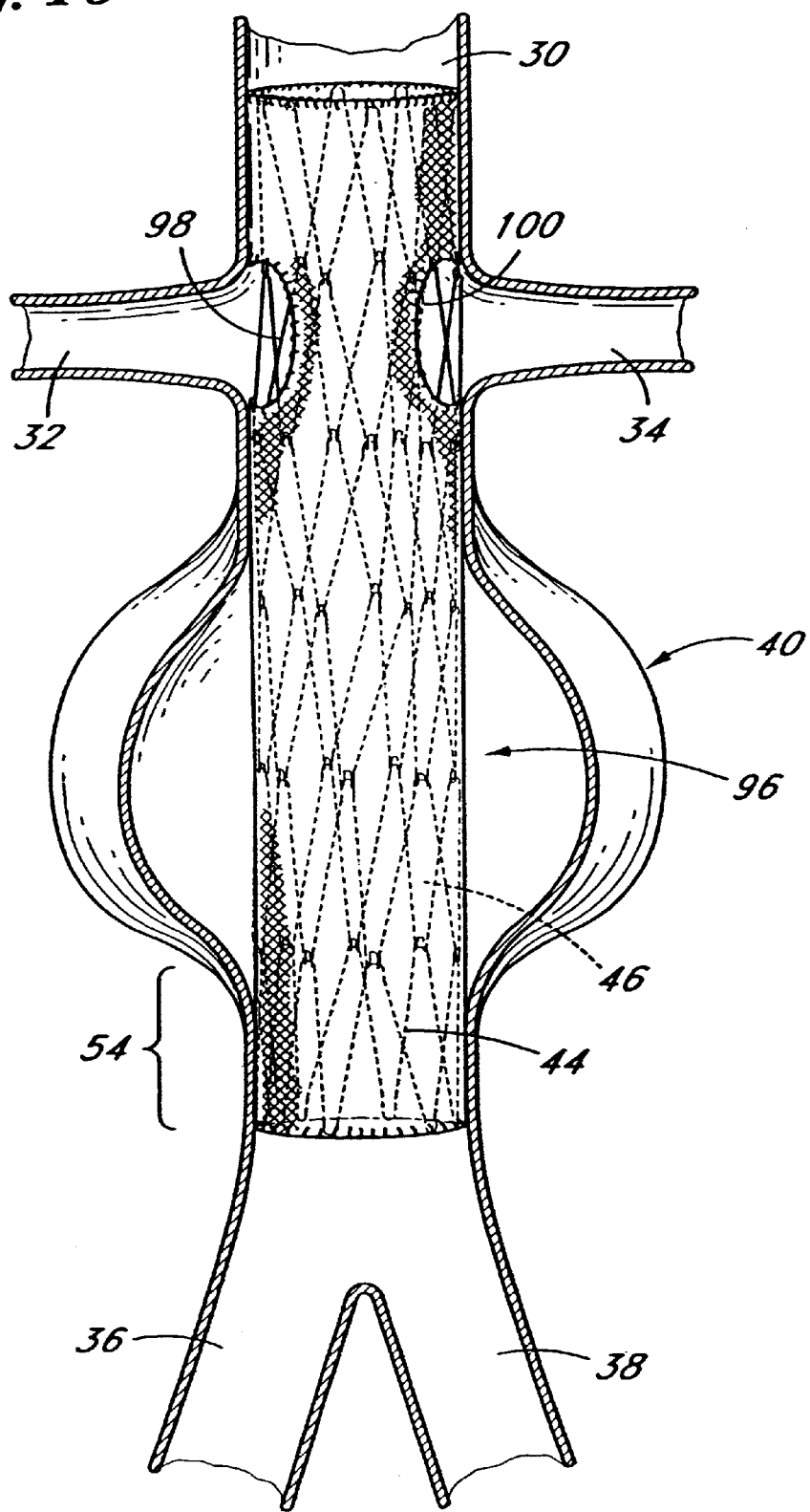
FIG. 16 is a schematic representation of a straight segment graft in accordance with a further embodiment of the present invention, with side openings to permit renal perfusion.

Referring to FIG. 16, there is illustrated a modified embodiment of the endovascular prosthesis 96 in accordance with the present invention. In the embodiment illustrated in FIG. 16, the endovascular prosthesis 96 is provided with a wire cage 46 having six axially aligned segments 54. As with the previous embodiments, however, the endovascular prosthesis 96 may be provided with anywhere from about 2 to about 10 or more axially spaced or adjacent segments 54, depending upon the clinical performance objectives of the particular embodiment.

The wire support 46 is provided with a tubular polymeric sleeve 44 as has been discussed. In the present embodiment, however, one or more lateral perfusion ports or openings are provided in the polymeric sleeve 44, such as a right renal artery perfusion port 98 and a left renal artery perfusion port 100 as illustrated.

Perfusion ports in the polymeric sleeve 44 may be desirable in embodiments of the endovascular prosthesis 96 in a variety of clinical contexts. For example, although FIGS. 1 and 16 illustrate a generally symmetrical aneurysm 40 positioned within a linear infrarenal portion of the abdominal aorta, spaced axially apart both from bilaterally symmetrical right and left renal arteries and bilaterally symmetrical right and left common iliacs, both the position and symmetry of the aneurysm 40 as well as the layout of the abdominal aortic architecture may differ significantly from patient to patient. As a consequence, the endovascular prosthesis 96 may need to extend across one or both of the renal arteries in order to adequately anchor the endovascular prosthesis 96 and/or span the aneurysm 40. The provision of one or more lateral perfusion ports or zones enables the endovascular prosthesis 96 to span the renal arteries while permitting perfusion therethrough, thereby preventing "stent jailing" of the renals. Lateral perfusion through the endovascular prosthesis 96 may also be provided, if desired, for a variety of other arteries including the second lumbar, testicular, inferior mesenteric, middle sacral, and alike as will be well understood to those of skill in the art.

The endovascular prosthesis 96 is preferably provided with at least one, and preferably two or more radiopaque markers, to facilitate proper positioning of the prosthesis 96 within the artery. In an embodiment having perfusion ports 98 and 100 such as in the illustrated design, the prosthesis 96 should be properly aligned both axially and rotationally, thereby requiring the ability to visualize both the axial and rotational position of the device. Alternatively, provided that the delivery catheter design exhibits sufficient torque transmission, the rotational orientation of the graft may be coordinated with an indexed marker on the proximal end of the catheter, so that the catheter may be rotated and determined by an external indicium of rotational orientation to be appropriately aligned with the right and left renal arteries.

In an alternative embodiment, the polymeric sleeve 44 extends across the aneurysm 40, but terminates in the infrarenal zone. In this embodiment, a proximal zone 55 on the prosthesis 96 comprises a wire cage 46 but no polymeric sleeve 44. In this embodiment, the prosthesis 96 still accomplishes the anchoring function across the renal 25 arteries, yet does not materially interfere with renal perfusion. Thus, the polymeric sleeve 44 may cover anywhere from about 50% to about 100% of the axial length of the prosthesis 96 depending upon the desired length of uncovered wire cage 46 such as for anchoring and/or lateral perfusion purposes. In particular embodiments, the polymeric sleeve 44 may cover within the range of from about 70% to about 80%, and, in one four segment embodiment having a single exposed segment, 75%, of the overall length of the prosthesis 96. The uncovered wire cage 46 may reside at only a single end of the prosthesis 96, such as for traversing the renal arteries. Alternatively, exposed portions of the wire cage 46 may be provided at both ends of the prosthesis such as for anchoring purposes.

In a further alternative, a two part polymeric sleeve 44 is provided. A first distal part spans the aneurysm 40, and has a proximal end which terminates distally of the renal arteries. A second, proximal part of the polymeric sleeve 44 is carried by the proximal portion of the wire cage 46 which is positioned superiorly of the renal arteries. This leaves an annular lateral flow path through the side wall of the vascular prosthesis 96, which can be axially aligned with the renal arteries, without regard to rotational orientation.

The axial length of the gap between the proximal and distal segments of polymeric sleeve 44 can be adjusted, depending upon the anticipated cross-sectional size of the ostium of the renal artery, as well as the potential axial misalignment between the right and left renal arteries. Although the right renal artery 32 and left renal artery 34 are illustrated in FIG. 16 as being concentrically disposed on opposite sides of the abdominal aorta, the take off point for the right or left renal arteries from the abdominal aorta may be spaced apart along the abdominal aorta as will be familiar to those of skill in the art. In general, the diameter of the ostium of the renal artery measured in the axial direction along the abdominal aorta falls within the range of from about 7 mm to about 20 mm for a typical adult patient.

Prior art procedures presently use a 7 mm introducer (18 French) which involves a surgical procedure for introduction of the graft delivery device. Embodiments of the present invention can be constructed having a 16 French or 15 French or 14 French or smaller profile (e.g. 3–4 mm) thereby enabling placement of the endoluminal vascular prosthesis of the present invention by way of a percutaneous procedure. In addition, the endoluminal vascular prosthesis of the present invention does not require a post implantation balloon dilatation, can be constructed to have minimal axial shrinkage upon radial expansion.

Figure 17:
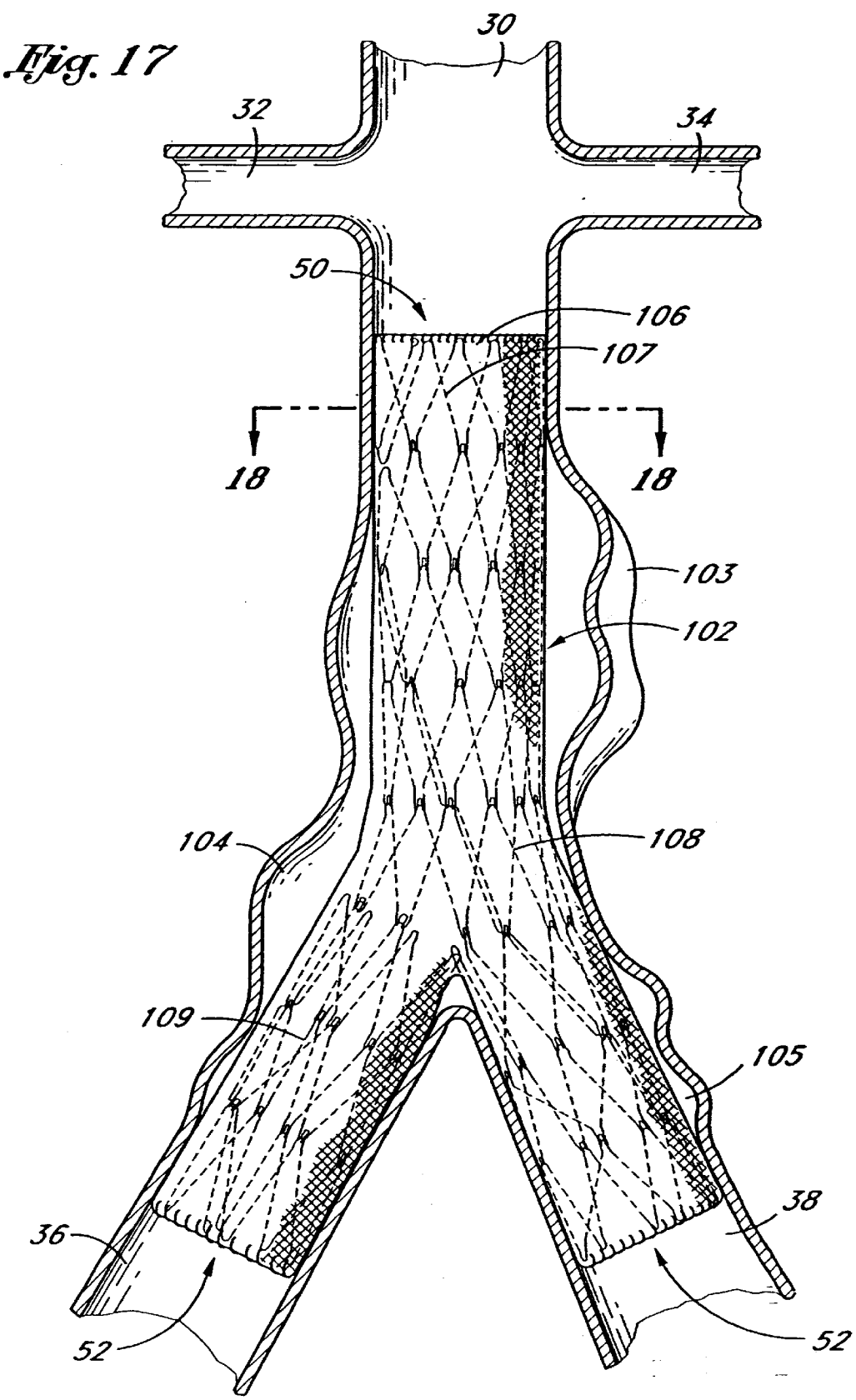
FIG. 17 is a schematic representation of a bifurcated vascular prosthesis in accordance with the present invention, positioned at the bifurcation between the abdominal aorta and the right and left common iliac arteries.

Referring to FIG. 17, there is disclosed a schematic representation of the abdominal part of the aorta and its principal branches as in FIG. 1. An expanded bifurcated endoluminal vascular prosthesis 102, in accordance with the present invention, is illustrated spanning the aneurysms 103, 104 and 105. The endoluminal vascular prosthesis 102 includes a polymeric sleeve 106 and a tubular wire support 107, which are illustrated in situ in FIG. 17. The sleeve 106 and wire support 107 are more readily visualized in the exploded view shown in FIG. 19. The endoluminal prosthesis 102 illustrated and described herein depicts an embodiment in which the polymeric sleeve 106 is situated concentrically outside of the tubular wire support 107. However, other embodiments may include a sleeve situated instead concentrically inside the wire support or on both of the inside and the outside of the wire support. Alternatively, the wire support may be embedded within a polymeric matrix which makes up the sleeve. Regardless of whether the sleeve 106 is inside or outside the wire support 107, the sleeve may be attached to the wire support by any of a variety of means, as has been previously discussed.

The tubular wire support 107 comprises a primary component 108 for traversing the aorta and a first iliac, and a branch component 109 for extending into the second iliac. The primary component 108 may be formed from a continuous single length of wire, throughout both the aorta trunk portion and the iliac branch portion. See FIGS. 19 and 20.

Alternatively, each iliac branch component can be formed separately from the aorta trunk portion. Construction of the graft from a three part cage conveniently facilitates the use of different gauge wire in the different components (e.g. 14 gauge main trunk and 10 gauge branch components).

Figure 20:
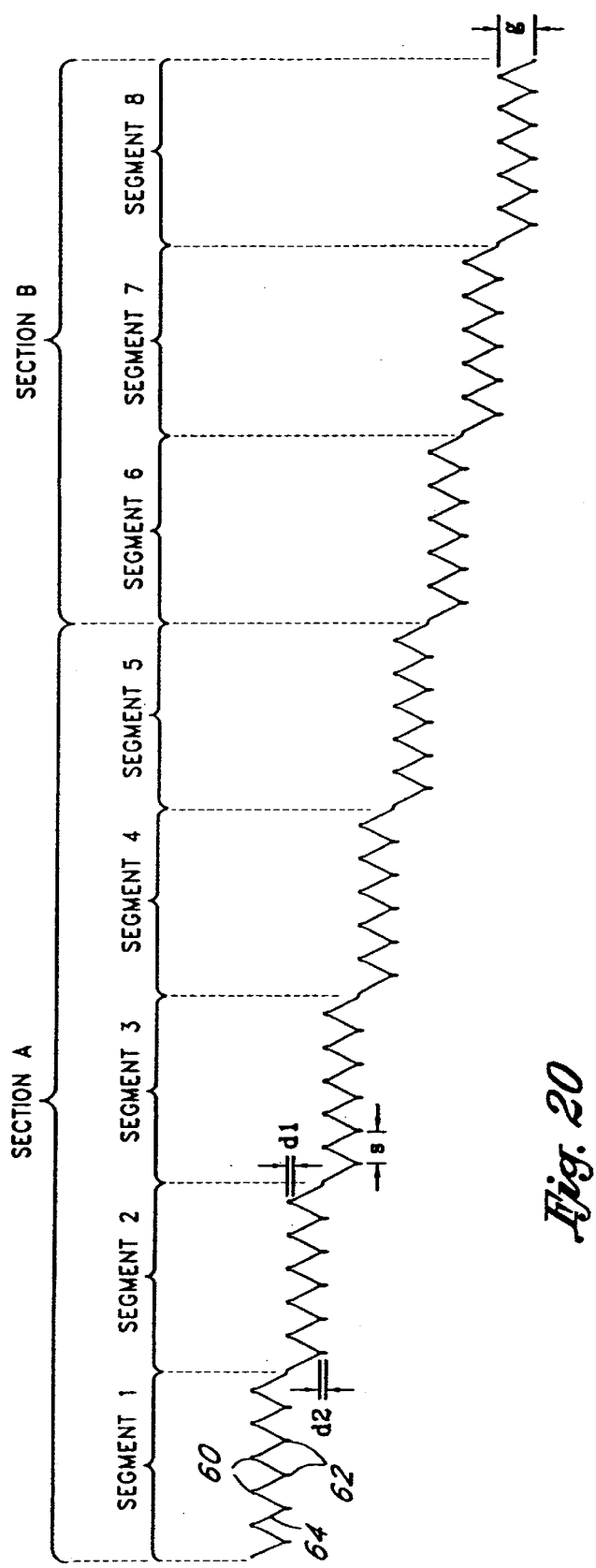
FIG. 20 is a plan view of formed wire useful for rolling about an axis into an aortic trunk segment and a first iliac branch segment support structure in accordance with the present invention.

The wire support 107 is preferably formed in a plurality of discrete segments, connected together and oriented about a common axis. In FIG. 20, Section A corresponds to the aorta trunk portion of the primary component 108, and includes segments 1–5. Segments 6–8 (Section B) correspond to the iliac branch portion of the primary component 108.

In general, each of the components of the tubular wire support 107 can be varied considerably in diameter, length, and expansion coefficient, depending upon the intended application. For implantation within a typical adult, the aorta trunk portion (section A) of primary component 108 will have a length within the range of from about 5 cm to about 12 cm, and, typically within the range of from about 9 cm to about 10 cm. The unconstrained outside expanded diameter of the section A portion of the primary component 108 will typically be within the range of from about 20 mm to about 40 mm. The unconstrained expanded outside diameter of the section A portion of primary component 108 can be constant or substantially constant throughout the length of section A, or can be tapered from a relatively larger diameter at the proximal end to a relatively smaller diameter at the bifurcation. In general, the diameter of the distal end of section A will be on the order of no more than about 95% and, preferably, no more than about 85% of the diameter of the proximal end of section A.

The right and left iliac portions, corresponding to section B on primary component 108 and section C will typically be bilaterally symmetrical. Section C length will generally be within the range of from about 1 cm to about 5 cm, and section C diameter will typically be within the range of from about 10 mm to about 20 mm.

Referring to FIG. 19, the wire cage 107 is dividable into a proximal zone 110, a central zone 111 and a distal zone 112. As has been discussed, the wire cage 107 can be configured to taper from a relatively larger diameter in the proximal zone 110 to a relatively smaller diameter in the distal zone 112. In addition, the wire cage 107 can have a transitional tapered and or stepped diameter within a given zone.

Referring to FIG. 20, there is illustrated a plan view of the single formed wire used for rolling about a longitudinal axis to produce a primary segment 108 having a five segment aorta section and a three segment iliac section. The formed wire exhibits distinct segments, each corresponding to an individual tubular segment in the tubular support. Additional details of the wire cage layout and construction can be found in U.S. Pat. No. 6,077,296 entitled Endoluminal Vascular Prosthesis, filed Mar. 4, 1998, the disclosure of which is incorporated in its entirety herein by reference.

Each segment has a repeating pattern of proximal bends 60 connected to corresponding distal bends 62 by wall sections 64 which extend in a generally zig-zag configuration when the segment is radially expanded, as has been discussed in connection with FIG. 3. Each segment is connected to the adjacent segment through a connector 66, and one or more links 70 as has been discussed in connection with FIGS. 5–12. The connector 66 in the illustrated embodiment comprises two wall sections 64 which connect a proximal bend 60 on a first segment with a distal bend 62 on a second, adjacent segment. The connector 66 may additionally be provided with a connector bend 68, which may be used to impart increased radial strength to the graft and/or provide a tie site for a circumferentially extending suture.

In the illustrated embodiment, section A is intended for deployment within the aorta whereas section B is intended to be deployed within a first iliac. Thus, section B will preferably have a smaller expanded diameter than section A. This may be accomplished by providing fewer proximal and distal bends 60, 62 per segment in section B or in other manners as will be apparent to those of skill in the art in view of the disclosure herein. In the illustrated embodiment, section B has one fewer proximal bend 60 per segment than does each segment in section A. This facilitates wrapping of the wire into a tubular prosthesis cage such as that illustrated in FIG. 19, so that the iliac branch has a smaller diameter than the aorta branch. At the bifurcation, an opening remains for connection of the second iliac branch. The second branch is preferably formed from a section of wire in accordance with the general principles discussed above, and in a manner that produces a similarly dimensioned wire cage as that produced by section B. The second iliac branch (section C) may be attached at the bifurcation to section A and/or section B in any of a variety of manners, to provide a secure junction therebetween. In one embodiment, one or two of the proximal bends 60 on section C will be secured to the corresponding distal bends 62 on the distal most segment of section A. Attachment may be accomplished such as through the use of a circumferentially threaded suture, through links 70 as has been discussed previously, through soldering or other attachment means. The attachment means will be influenced by the desirable flexibility of the graft at the bifurcation, which will in turn be influenced by the method of deployment of the vascular graft as will be apparent to those of skill in the art in view of the disclosure herein.

Figure 21:
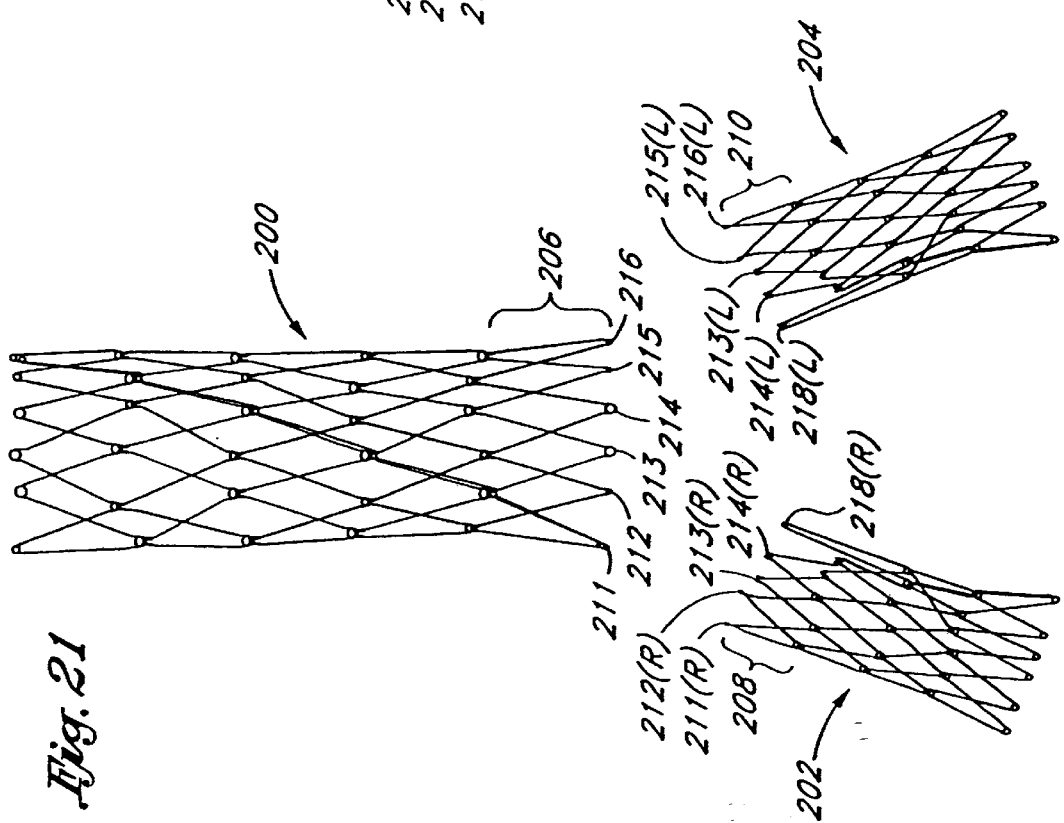
FIG. 21 is a schematic representation of another embodiment of the wire support structure for the bifurcated vascular prosthesis of the present invention, showing a main body support structure and separate branch support structures.

Referring to FIG. 21, there is disclosed an exploded schematic representation of a hinged or articulated variation in the tubular wire support structure for a bifurcated graft in accordance with present invention. The tubular wire support comprises a main body, or aortic trunk portion 200 and right 202 and left 204 iliac branch portions. Right and left designations correspond to the anatomic designations of right and left common iliac arteries. The proximal end 206 of the aortic trunk portion 200 has apexes 211–216 adapted for connection with the complementary apexes on the distal ends 208 and 210 of the right 202 and left 204 iliac branch portions, respectively. Complementary pairing of apexes is indicated by the shared numbers, wherein the right branch portion apexes are designated by (R) and the left branch portion apexes are designated by (L). Each of the portions may be formed from a continuous single length of wire. See FIG. 23.

Figure 22:
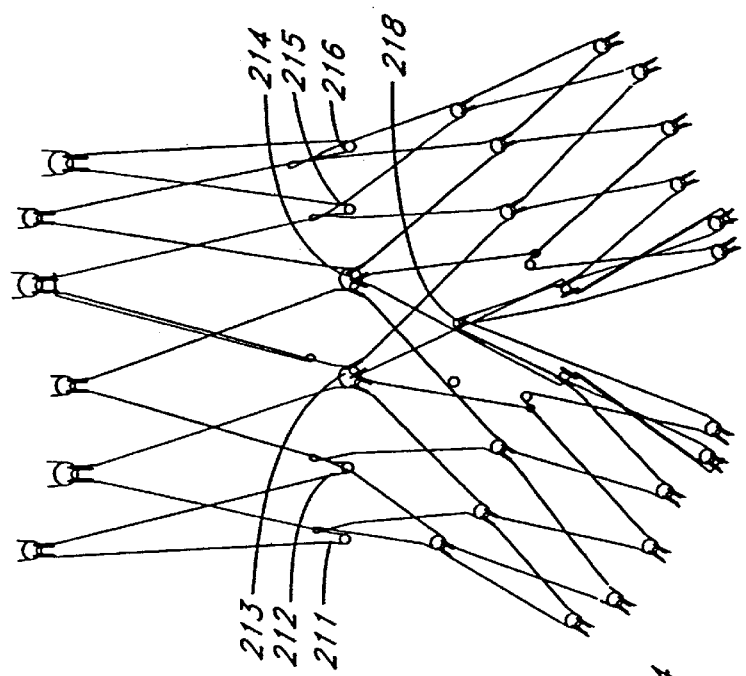
FIG. 22 is a schematic representation of the three-part wire support structure as in FIG. 21, illustrating the sliding articulation between the branch supports and the main body support.

Referring to FIG. 22, the assembled articulated wire support structure is shown. The central or medial apex 213 in the foreground (anterior) of the aortic trunk portion 200 is linked with 213(R) on the right iliac portion 202 and 213(L) on the left iliac portion 204. Similarly, the central apex 214 in the background (posterior) is linked with 214(R) on the right iliac portion 202 and 214(L) on the left iliac portion 204. Each of these linkages has two iliac apexes joined with one aortic branch apex. The linkage configurations may be of any of the variety described above in FIG. 7A–D. The medial most apexes 218 (R) and (L) of the iliac branch portions 202 and 204 are linked together, without direct connection with the aortic truck portion 200.

The medial apexes 213 and 214 function as pivot points about which the right and left iliac branches 202, 204 can pivot to accommodate unique anatomies. Although the right and left iliac branches 202, 204 are illustrated at an angle of about 45° to each other, they are articulable through at least an angle of about 90° and preferably at least about 120°. The illustrated embodiment allows articulation through about 180° while maintaining patency of the central lumen. To further improve patency at high iliac angles, the apexes 213 and 214 can be displaced proximally from the transverse plane which roughly contains apexes 211, 212, 215 and 216 by a minor adjustment to the fixture about which the wire is formed. Advancing the pivot point proximally relative to the lateral apexes (e.g., 211, 216) opens the unbiased angle between the iliac branches 202 and 204.

In the illustrated embodiment, the pivot point is formed by a moveable link between an eye on apex 213 and two apexes 213R and 213L folded therethrough. To accommodate the two iliac apexes 213R and 213L, the diameter of the eye at apex 213 may be slightly larger than the diameter of the eye on other apexes throughout the graft. Thus, for example, the diameter of the eye at apex 213 in one embodiment made from 0.014" diameter wire is about 0.059", compared to a diameter of about 0.020" for eyes elsewhere in the graft.

Although the pivot points (apexes 213, 214) in the illustrated embodiment are on the medial plane, they may be moved laterally such as, for example, to the axis of each of the iliac branches. In this variation, each iliac branch will have an anterior and a posterior pivot link on or about its longitudinal axis, for a total of four unique pivot links at the bifurcation. Alternatively, the pivot points can be moved as far as to lateral apexes 211 and 216. Other variations will be apparent to those of skill in the art in view of the disclosure herein.

To facilitate lateral rotation of the iliac branches 202, 204 about the pivot points and away from the longitudinal axis of the aorta trunk portion 200 of the graft, the remaining links between the aorta trunk portion 200 and the iliac branches 202, 204 preferably permit axial compression and expansion. In general, at least one and preferably several links lateral to the pivot point in the illustrated embodiment permit axial compression or shortening of the graft to accommodate lateral pivoting of the iliac branch. If the pivot point is moved laterally from the longitudinal axis of the aorta portion of the graft, any links medial of the pivot point preferably permit axial elongation to accommodate lateral rotation of the branch. In this manner, the desired range of rotation of the iliac branches may be accomplished with minimal deformation of the wire, and with patency of the graft optimized throughout the angular range of motion.

To permit axial compression substantially without deformation of the wire, the lateral linkages, 211 and 212 for the right iliac, and 215 and 216 for the left iliac, may be different from the previously described apex-to-apex linkage configurations. The lateral linkages are preferably slidable linkages, wherein a loop formed at the distal end of the iliac apex slidably engages a strut of the corresponding aortic truck portion. The loop and strut orientation may be reversed, as will be apparent to those of skill in the art. Interlocking "elbows" without any distinct loop may also be used. Such an axially compressible linkage on the lateral margins of the assembled wire support structure allow the iliac branch portions much greater lateral flexibility, thereby facilitating placement in patients who often exhibit a variety of iliac branch asymmetries and different angles of divergence from the aortic trunk.

Figure 23:
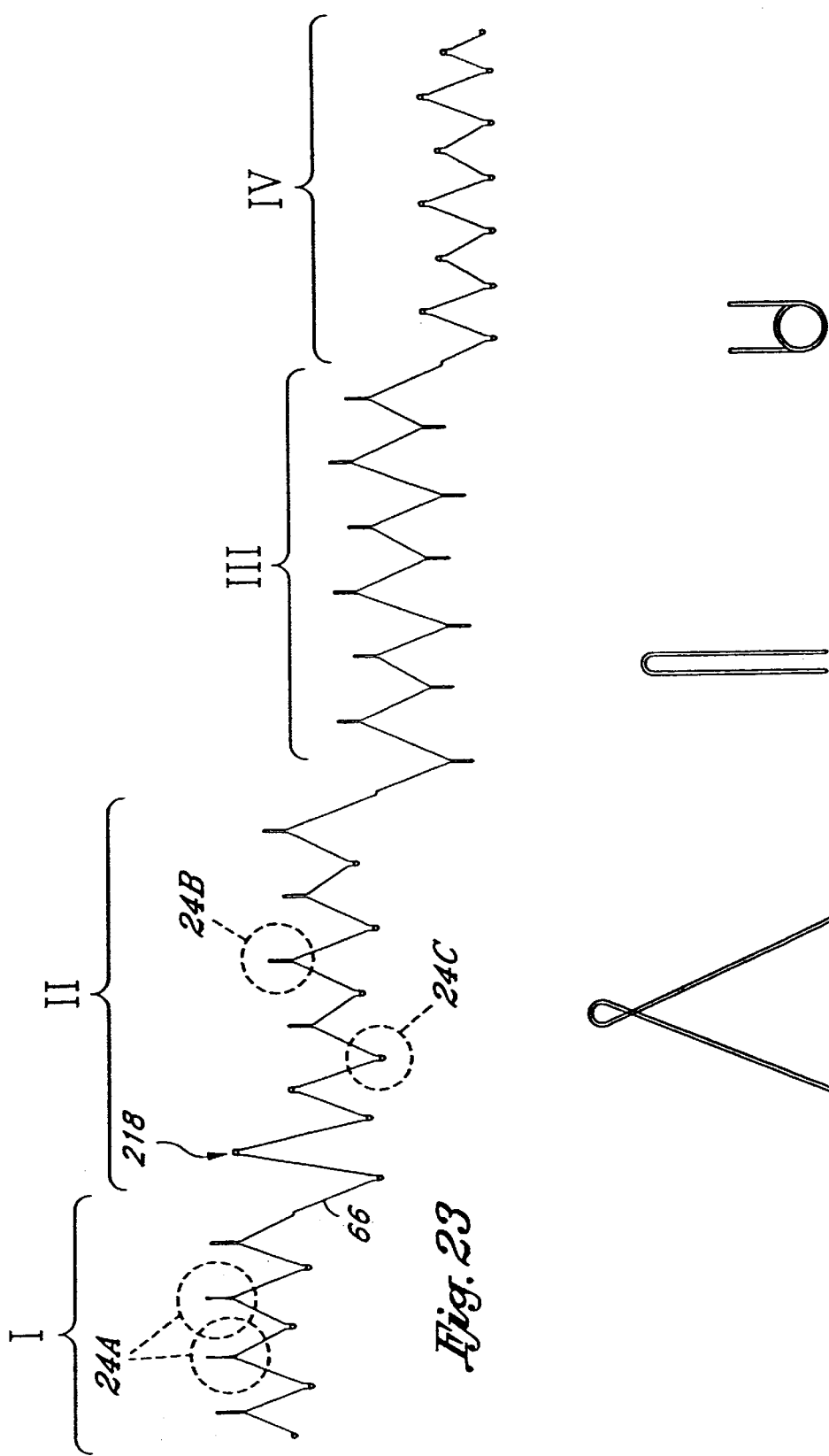
FIG. 23 is a plan view of formed wire useful for rolling about an axis to form a branch support structure in accordance with the three-part support embodiment of the present invention shown in FIG. 21.
Figure 24A:
FIGS. 24A, 24B and 24C are enlargements of the apexes delineated by lines A, B and C, respectively, in FIG. 23.

Referring to FIG. 23, there is illustrated a plan view of a single formed wire used for rolling about a longitudinal axis to produce a four segment straight tubular wire support for an iliac limb. The formed wire exhibits distinct segments, each corresponding to an individual tubular segment in the tubular supports 202 or 204 (See FIG. 21). The distal segment I, is adapted to articulate with the aortic trunk portion 200 and the adjacent iliac limb portion. The distal segment (I) has two apexes (e.g. corresponding to 211 and 212 on the right iliac portion 202 in FIG. 21) which form a loop adapted to slidably engage a strut in the lateral wall of the aortic portion. These articulating loops (A) are enlarged in FIG. 24A. As discussed above, the loops are preferably looped around a strut on the corresponding apex of the proximal aortic segment to provide a sliding linkage.

The apex 218 is proximally displaced relative to the other four apexes in the distal segment (I). Apex 218 (R or L) is designed to link with the complementary 218 apex on the other iliac branch portion (See FIG. 22). The apex 218 in the illustrated embodiment is formed adjacent or near an inter-segment connector 66, which extends proximally from the distal segment.

Figure 24B:
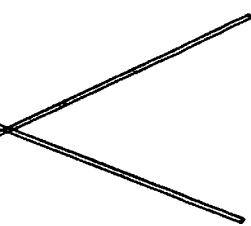

The other apexes on the distal segment (I) of an iliac limb are designed to link with a loop on the corresponding apex of the proximal aortic segment. Because many variations of this linkage are consistent with the present invention (See FIGS. 7A–D), the form of the corresponding apexes may vary. In a preferred variation, the apexes (B) form a narrow U-shape, having an inside diameter of about 0.019 inches in an embodiment made from 0.012 inch Conichrome wire (tensile strength 300 ksi minimum) as illustrated in FIG. 24B. The U-shaped, elongated axial portion of the apex shown in FIG. 24B permits the apex to be wrapped through and around a corresponding loop apex of the proximal aortic segment. This type of linkage is discussed in greater detail above in connection with FIGS. 5 and 6.

In more general terms, the wire support illustrated in FIGS. 21 and 22 comprises a main body support structure formed from one or more lengths of wire and having a proximal end, a distal end and a central lumen extending along a longitudinal axis. The wire support also comprises a first branch support structure formed from one or more lengths of wire and having a proximal end, a distal end and a central lumen therethrough. The first branch support structure is pivotably connected to the proximal end of the main body support structure. The tubular wire support further comprises a second branch support structure formed from one or more lengths of wire and having a proximal end, a distal end and a central lumen extending therethrough. The distal end of the second branch support structure is pivotably connected to the proximal end of the main body support structure.

Further, the distal ends of the first and second branch structures may be joined together by a flexible linkage, formed for example between apexes 218(R) and 218(L) in FIG. 21. By incorporating a medial linkage between the two branch support structures and pivotable linkages with the main trunk, the first and second branch support structures can hinge laterally outward from the longitudinal axis without compromising the volume of the lumen. Thus, the branches may enjoy a wide range of lateral movement, thereby accommodating a variety of patient and vessel heterogeneity. Additional corresponding apexes between the main trunk and each iliac branch may also be connected, or may be free floating within the outer polymeric sleeve. Axially compressible lateral linkages, discussed above and illustrated in FIG. 22, may optionally be added.

The proximal apexes (C) of the iliac limb portions are adapted to link with the distal apexes of the next segment.

Figure 24C:

These proximal apexes preferably form loops, such as those illustrated in FIG. 24C, wherein the elongated axial portions of the corresponding proximal apex in the adjacent segment can wrap around the loop, thereby providing flexibility of the graft, as discussed above for FIGS. 5 and 6.

The wire may be made from any of a variety of different alloys and wire diameters or non-round cross-sections, as has been discussed. In one embodiment of the bifurcation graft, the wire gauge remains substantially constant throughout section A of the primary component 49 and steps down to a second, smaller cross-section throughout section B of primary component 108.

A wire diameter of approximately 0.018 inches may be useful in the aorta trunk portion of a graft having five segments each having 2.0 cm length per segment, each segment having six struts intended for use in the aorta, while a smaller diameter such as 0.012 inches might be useful for segments of the graft having 6 struts per segment intended for the iliac artery.

In one embodiment of the present invention, the wire diameter may be tapered throughout from the proximal to distal ends of the section A and/or section B portions of the primary component 108. Alternatively, the wire diameter may be tapered incremental or stepped down, or stepped up, depending on the radial strength requirements of each particular clinical application. In one embodiment, intended for the abdominal aortic artery, the wire has a cross-section of about 0.018 inches in the proximal zone 110 and the wire tapers down regularly or in one or more steps to a diameter of about 0.012 inches in the distal zone 112 of the graft 102. End point dimensions and rates of taper can be varied widely, within the spirit of the present invention, depending upon the desired clinical performance.

In general, in the tapered or stepped wire embodiments, the diameter of the wire in the iliac branches is no more than about 80% of the diameter of the wire in the aortic trunk. This permits increased flexibility of the graft in the region of the iliac branches, which has been determined by the present inventors to be clinically desirable.

The collapsed prosthesis in accordance with the present invention has a diameter in the range of about 2 to about 10 mm. Preferably, the maximum diameter of the collapsed prosthesis is in the range of about 3 to 6 mm (12 to 18 French). Some embodiments of the delivery catheter including the prosthesis will be in the range of from 18 to 20 or 21 French; other embodiments will be as low as 19 F, 16 F, 14 F, or smaller. After deployment, the expanded endoluminal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

The self expandable bifurcation graft of the present invention can be deployed at a treatment site in accordance with any of a variety of techniques as will be apparent to those of skill in the art. One such technique is disclosed in copending patent application Ser. No. 08/802,478 entitled Bifurcated Vascular Graft and Method and Apparatus for Deploying Same, filed Feb. 20, 1997, the disclosure of which is incorporated in its entirety herein by reference.

Figure 25:
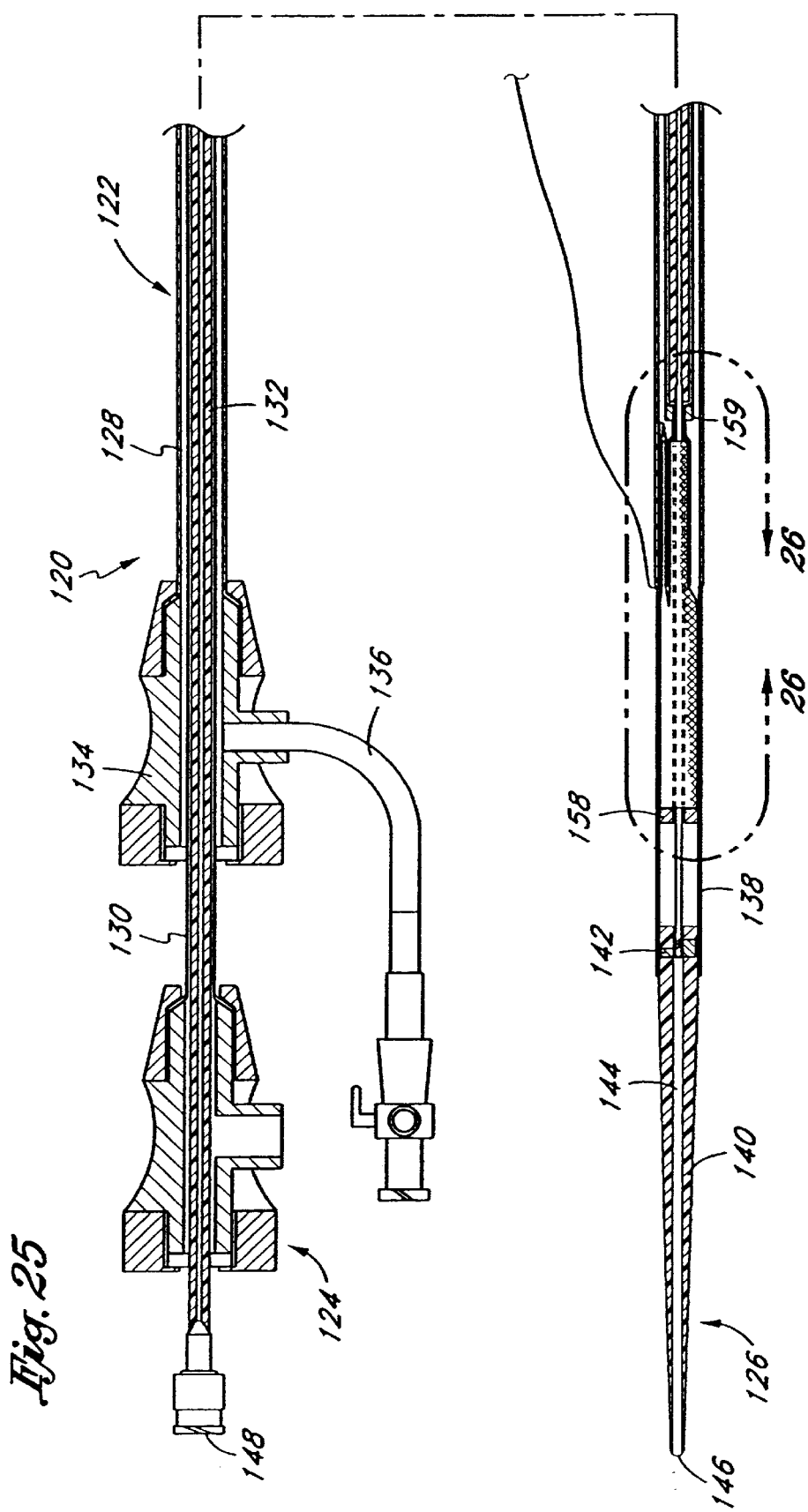
FIG. 25 is side elevational cross-section of a bifurcation graft delivery catheter in accordance with the present invention.

A partial cross-sectional side elevational view of one deployment apparatus 120 in accordance with the present invention is shown in FIG. 25. The deployment apparatus 120 comprises an elongate flexible multicomponent tubular body 122 having a proximal end 124 and a distal end 126. The tubular body 122 and other components of this system can be manufactured in accordance with any of a variety of techniques well known in the catheter manufacturing field. Suitable materials and dimensions can be readily selected taking into account the natural anatomical dimensions in the iliacs and aorta, together with the dimensions of the desired percutaneous access site.

The elongate flexible tubular body 122 comprises an outer sheath 128 which is axially movably positioned upon an intermediate tube 130. A central tubular core 132 is axially movably positioned within the intermediate tube 130. In one embodiment, the outer tubular sheath comprises extruded PTFE, having an outside diameter of about 0.250" and an inside diameter of about 0.230". The tubular sheath 128 is provided at its proximal end with a manifold 134, having a hemostatic valve 136 thereon and access ports such as for the infusion of drugs or contrast media as will be understood by those of skill in the art.

The outer tubular sheath 128 has an axial length within the range of from about 40" to about 55", and, in one embodiment of the deployment device 120 having an overall length of 110 cm, the axial length of the outer tubular sheath 128 is about 52 cm and the outside diameter is no more than about 0.250". Thus, the distal end of the tubular sheath 128 is located at least about 16 cm proximally of the distal end 126 of the deployment catheter 120 in stent loaded configuration.

As can be seen from FIGS. 26 and 27–28, proximal retraction of the outer sheath 128 with respect to the intermediate tube 130 will expose the compressed iliac branches of the graft, as will be discussed in more detail below.

A distal segment of the deployment catheter 120 comprises an outer tubular housing 138, which terminates distally in an elongate flexible tapered distal tip 140. The distal housing 138 and tip 140 are axially immovably connected to the central core 132 at a connection 142.

The distal tip 140 preferably tapers from an outside diameter of about 0.225" at its proximal end to an outside diameter of about 0.070" at the distal end thereof. The overall length of the distal tip 140 in one embodiment of the deployment catheter 120 is about 3". However, the length and rate of taper of the distal tip 140 can be varied depending upon the desired trackability and flexibility characteristics. The distal end of the housing 138 is secured to the proximal end of the distal tip 140 such as by thermal bonding, adhesive bonding, and/or any of a variety of other securing techniques known in the art. The proximal end of distal tip 140 is preferably also directly or indirectly connected to the central core 132 such as by a friction fit and/or adhesive bonding.

In at least the distal section of the catheter, the central core 132 preferably comprises a length of hypodermic needle tubing. The hypodermic needle tubing may extend throughout the length catheter to the proximal end thereof, or may be secured to the distal end of a proximal extrusion as illustrated for example in FIG. 22. A central guidewire lumen 144 extends throughout the length of the tubular central core 132, having a distal exit port 146 and a proximal access port 148 as will be understood by those of skill in the art.

Referring to FIGS. 26–28, a bifurcated endoluminal graft 150 is illustrated in a compressed configuration within the deployment catheter 120. The graft 150 comprises a distal aortic section 152, a proximal ipsilateral iliac portion 154, and a proximal contralateral iliac portion 156. The aortic trunk portion 152 of the graft 150 is contained within the tubular housing 138. Distal axial advancement of the central tubular core 132 will cause the distal tip 140 and housing 138 to advance distally with respect to the graft 150, thereby permitting the aortic trunk portion 152 of the graft 150 to expand to its larger, unconstrained diameter. Distal travel of the graft 150 is prevented by a distal stop 158 which is axially immovably connected to the intermediate tube 130. Distal stop 158 may comprise any of a variety of structures, such as an annular flange or component which is adhered to, bonded to or integrally formed with a tubular extension 160 of the intermediate tube 132. Tubular extension 160 is axially movably positioned over the hypotube central core 132.

The tubular extension 160 extends axially throughout the length of the graft 150. At the proximal end of the graft 150, a step 159 axially immovably connects the tubular extension 160 to the intermediate tube 130. In addition, the step 159 provides a proximal stop surface to prevent proximal travel of the graft 150 on the catheter 120. The function of step 159 can be accomplished through any of a variety of structures as will be apparent to those of skill in the art in view of the disclosure herein. For example, the step 159 may comprise an annular ring or spacer which receives the tubular extension 160 at a central aperture therethrough, and fits within the distal end of the intermediate tube 130. Alternatively, the intermediate tube 130 can be reduced in diameter through a generally conical section or shoulder to the diameter of tubular extension 160.

Proximal retraction of the outer sheath 128 will release the iliac branches 154 and 156 of the graft 150. The iliac branches 154 and 156 will remain compressed, within a first (ipsilateral) tubular sheath 162 and a second (contralateral) tubular sheath 164. The first tubular sheath 162 is configured to restrain the ipsilateral branch of the graft 150 in the constrained configuration, for implantation at the treatment site. The first tubular sheath 162 is adapted to be axially proximally removed from the iliac branch, thereby permitting the branch to expand to its implanted configuration. In one embodiment, the first tubular sheath 162 comprises a thin walled PTFE extrusion having an outside diameter of about 0.215" and an axial length of about 7.5 cm. A proximal end of the tubular sheath 162 is necked down such as by heat shrinking to secure the first tubular sheath 162 to the tubular extension 160. In this manner, proximal withdrawal of the intermediate tube 130 will in turn proximally advance the first tubular sheath 162 relative to the graft 150, thereby deploying the self expandable iliac branch of the graft 150.

The second tubular sheath 164 is secured to the contralateral guidewire 166, which extends outside of the tubular body 122 at a point 168, such as may be conveniently provided at the junction between the outer tubular sheath 128 and the distal housing 138. The second tubular sheath 164 is adapted to restrain the contralateral branch of the graft 150 in the reduced profile. In one embodiment of the invention, the second tubular sheath 164 has an outside diameter of about 0.215" and an axial length of about 7.5 cm. The second tubular sheath 164 can have a significantly smaller cross-section than the first tubular sheath 162, due to the presence of the tubular core 132 and intermediate tube 130 within the first iliac branch 154.

The second tubular sheath 164 is secured at its proximal end to a distal end of the contralateral guidewire 166. This may be accomplished through any of a variety of securing techniques, such as heat shrinking, adhesives, mechanical interfit and the like. In one embodiment, the guidewire is provided with a knot or other diameter enlarging structure to provide an interference fit with the proximal end of the second tubular sheath 156, and the proximal end of the second tubular sheath 156 is heat shrunk and/or bonded in the area of the knot to provide a secure connection. Any of a variety of other techniques for providing a secure connection between the contralateral guidewire 166 and tubular sheath 156 can readily be used in the context of the present invention as will be apparent to those of skill in the art in view of the disclosure herein. The contralateral guidewire 166 can comprise any of a variety of structures, including polymeric monofilament materials, braided or woven materials, metal ribbon or wire, or conventional guidewires as are well known in the art.

In use, the free end of the contralateral guidewire 166 is percutaneously inserted into the arterial system, such as at a first puncture in a femoral artery. The contralateral guidewire is advanced through the corresponding iliac towards the aorta, and crossed over into the contralateral iliac in accordance with cross over techniques which are well known in the art. The contralateral guidewire is then advanced distally down the contralateral iliac where it exits the body at a second percutaneous puncture site.

Figure 30:
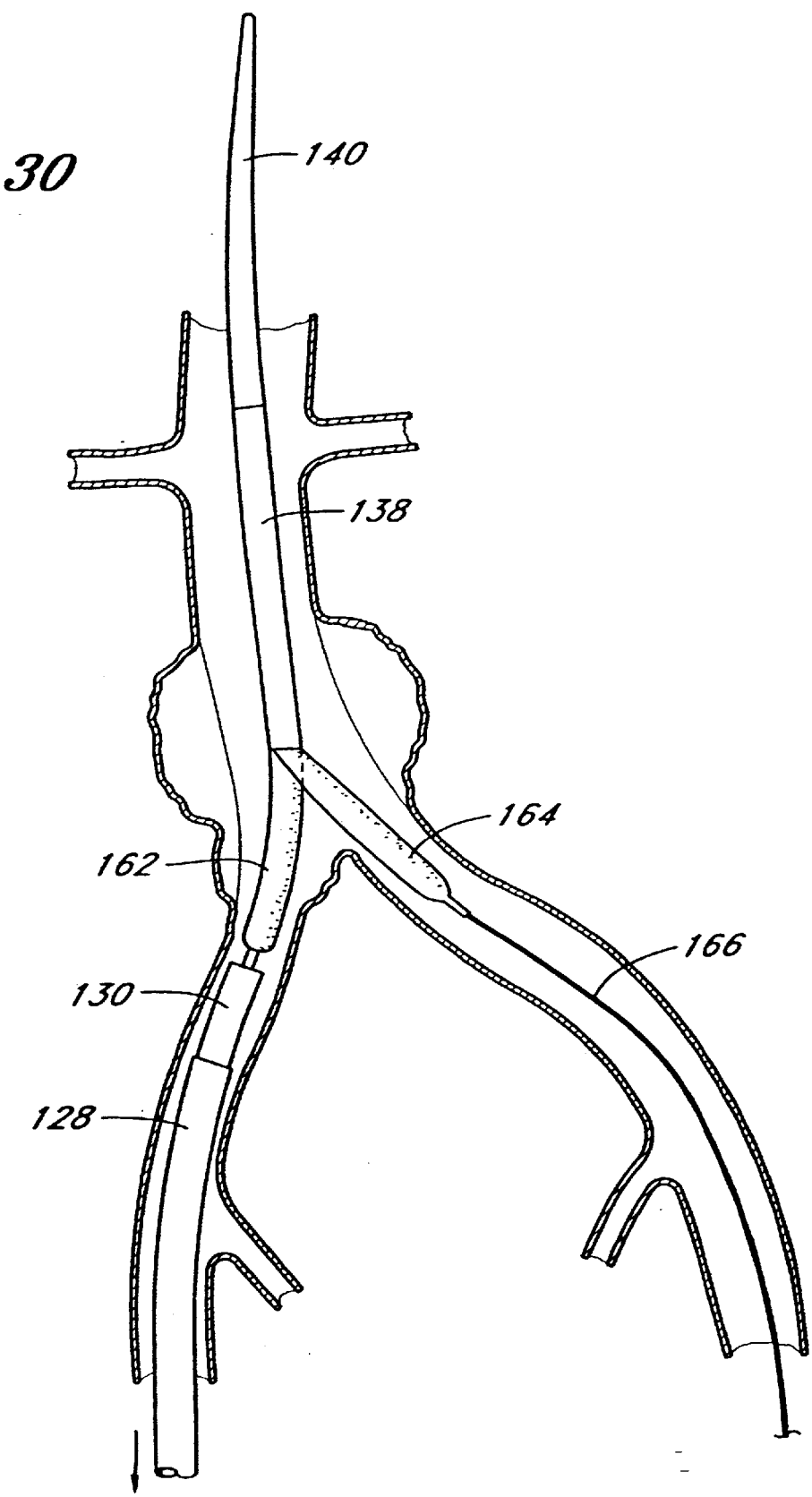
FIG. 30 is a schematic representation as in FIG. 29, with the outer sheath proximally retracted and the compressed iliac branches of the graft moving into position within the iliac arteries.

The deployment catheter 120 is thereafter percutaneously inserted into the first puncture, and advanced along a guidewire (e.g. 0.035 inch) through the ipsilateral iliac and into the aorta. As the deployment catheter 120 is transluminally advanced, slack produced in the contralateral guidewire 166 is taken up by proximally withdrawing the guidewire 166 from the second percutaneous access site. In this manner, the deployment catheter 120 is positioned in the manner generally illustrated in FIG. 29. Referring to FIG. 30, the outer sheath 128 is proximally withdrawn while maintaining the axial position of the overall deployment catheter 120, thereby releasing the first and second iliac branches of the graft 150. Proximal advancement of the deployment catheter 120 and contralateral guidewire 166 can then be accomplished, to position the iliac branches of the graft 150 within the iliac arteries as illustrated.

Figure 31:
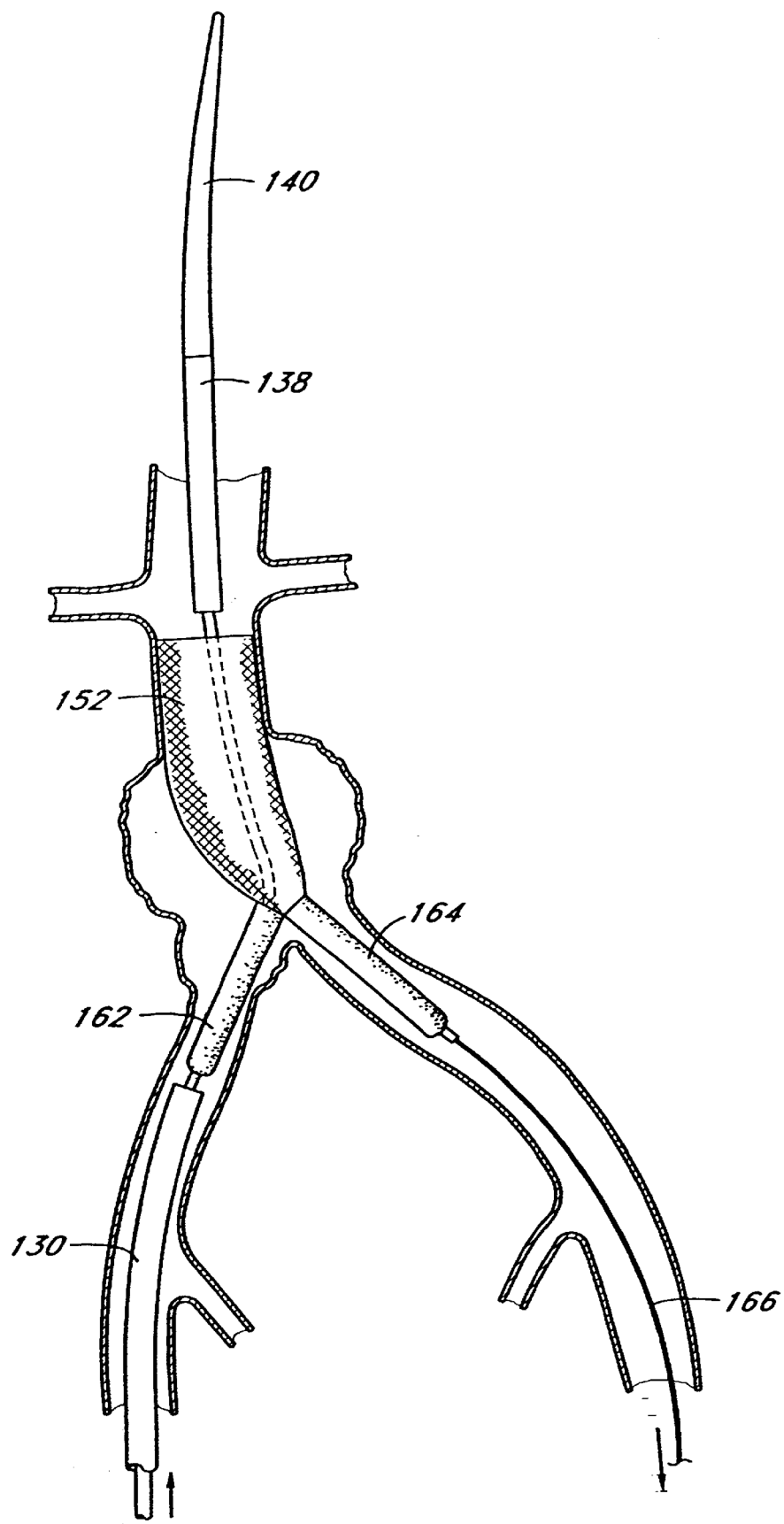
FIG. 31 is a schematic representation as in FIG. 30, with the compressed iliac branches of the graft within the iliac arteries, and the main aortic trunk of the graft deployed within the aorta.
Figure 32:
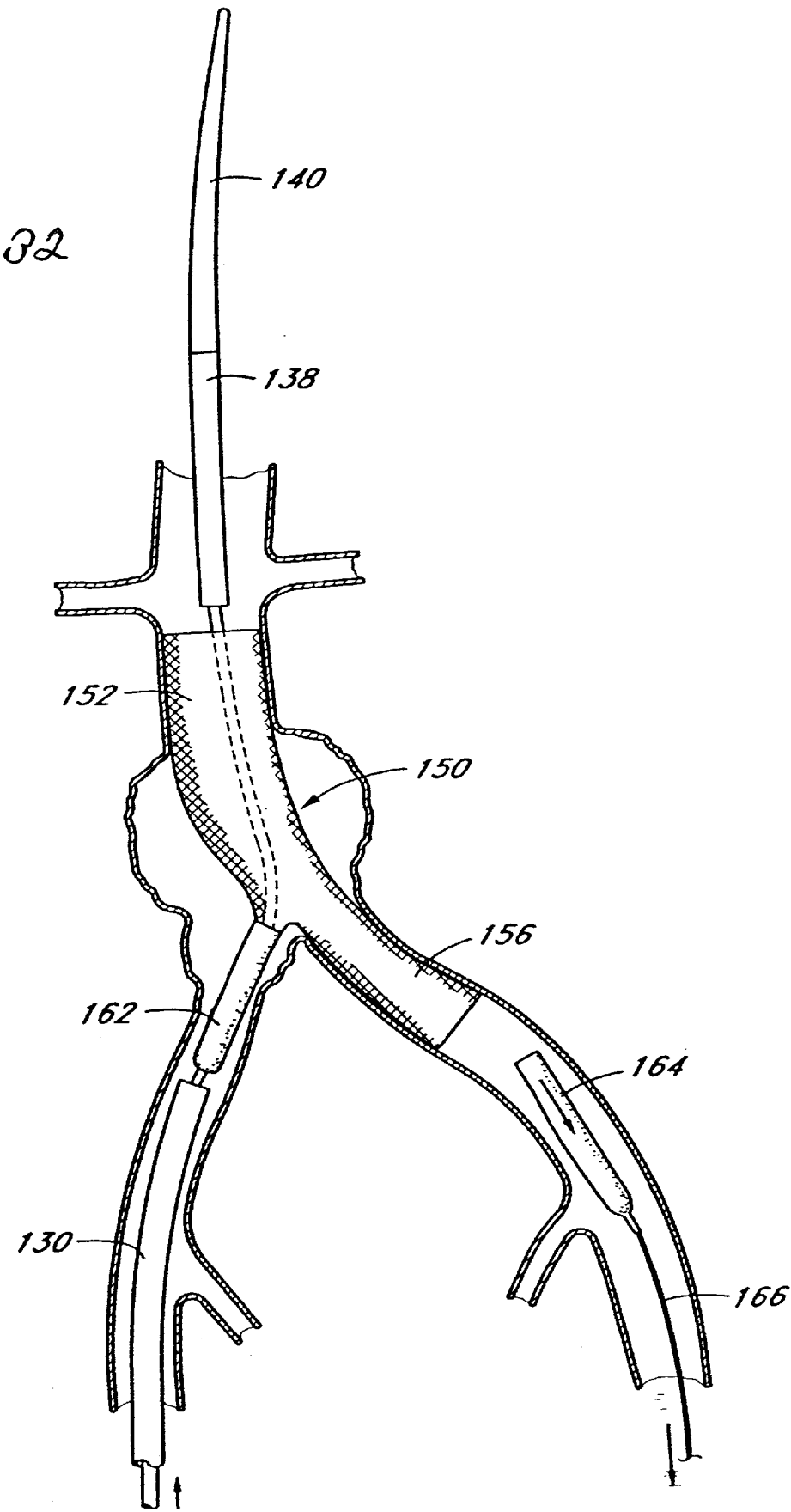
FIG. 32 is a schematic representation as in FIG. 31, with the contralateral iliac branch of the graft deployed.

Referring to FIG. 31, the central core 132 is distally advanced thereby distally advancing the distal housing 138 as has been discussed. This exposes the aortic trunk of the graft 150, which deploys into its fully expanded configuration within the aorta. As illustrated in FIG. 32, the contralateral guidewire 166 is thereafter proximally withdrawn, thereby by proximally withdrawing the second sheath 164 from the contralateral iliac branch 156 of the graft 150. The contralateral branch 156 of the graft 150 thereafter self expands to fit within the iliac artery. The guidewire 166 and sheath 164 may thereafter be proximally withdrawn and removed from the patient, by way of the second percutaneous access site.

Figure 33:
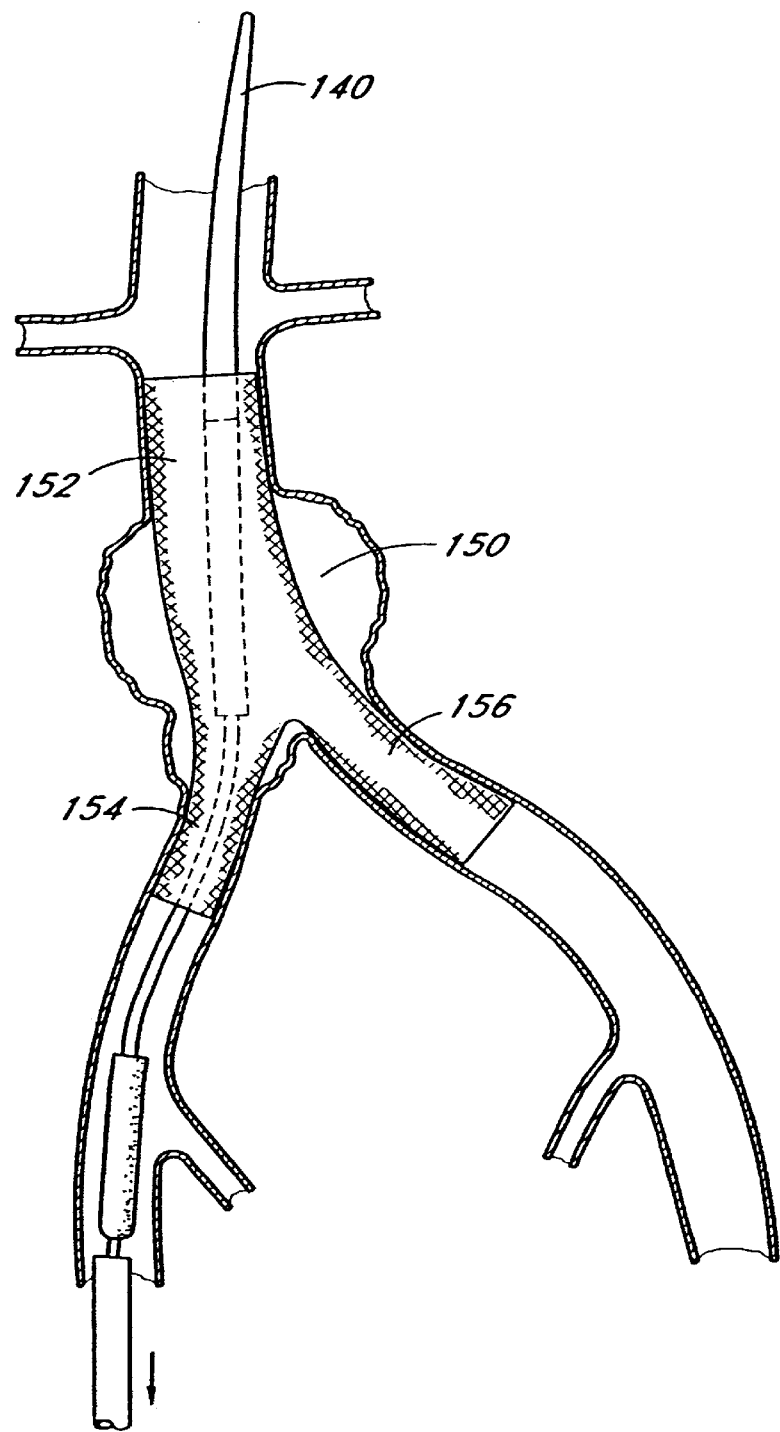
FIG. 33 is a schematic representation as in FIG. 32, following deployment of the ipsilateral branch of the graft.

Thereafter, the deployment catheter 120 may be proximally withdrawn to release the ipsilateral branch 154 of the graft 150 from the first tubular sheath 162 as shown in FIG. 33. Following deployment of the ipsilateral branch 154 of the prosthesis 150, a central lumen through the aortic trunk 152 and ipsilateral branch 154 is sufficiently large to permit proximal retraction of the deployment catheter 120 through the deployed bifurcated graft 150. The deployment catheter 120 may thereafter be proximally withdrawn from the patient by way of the first percutaneous access site.

Figure 34C:
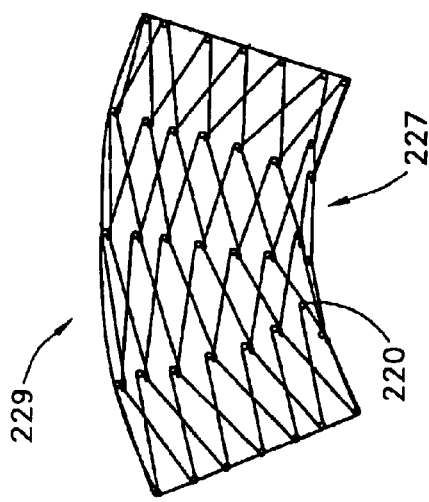
FIG. 34c is a side elevational view of the graft of FIG. 34a, having a radius of curvature.
Figure 34D:
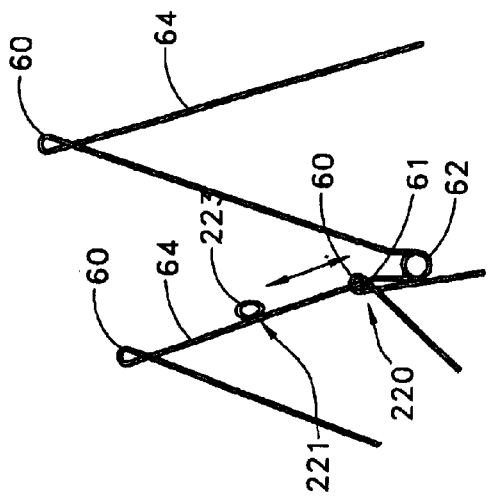
FIG. 34d is a detail view as in FIG. 34b, illustrating a lock for limiting axial compression of the sliding link.
Figure 34B:
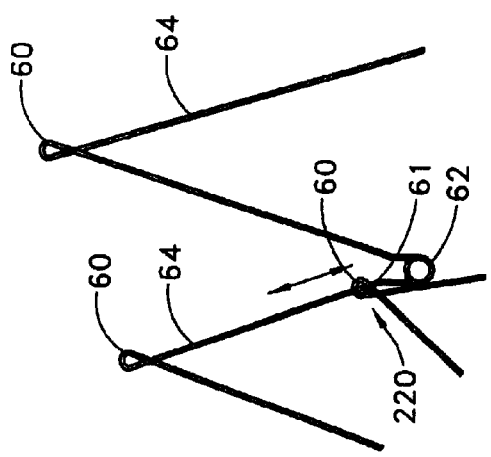
Figure 34A:
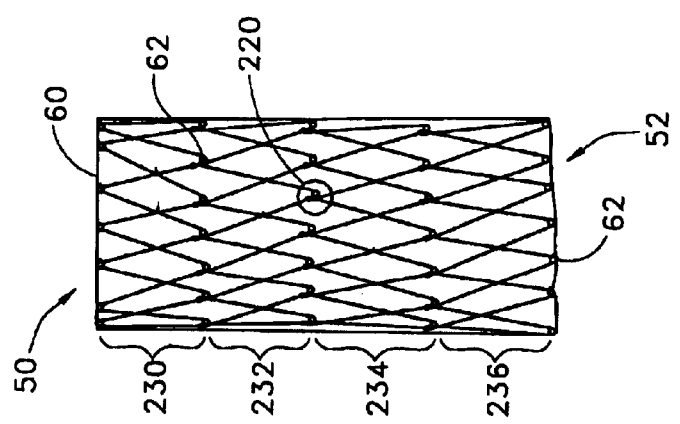
FIG. 34a is a side elevational view of a flexible straight graft in accordance with the present invention.

Referring to FIGS. 34*a*–34*c,* there is illustrated a flexible, straight graft design in accordance with a further aspect of the present invention. In this configuration, the wire cage may be flexed around a bend by allowing axial compression on an inside radius 227 compared to an outside radius 229, as seen in FIG. 34*c.* Axial compression on the inside radius 227 is enabled by the provision of a plurality of sliding links 220, one embodiment of which is illustrated in FIG. 34b. In general, the sliding link 220 enables the connection between a proximal bend 60 and a corresponding distal bend 62 to be compressible in the axial direction while maintaining the radial strength and radial expandability of the graft.

In the illustrated embodiment, this is accomplished by looping the proximal bend 60 around a wall section 64 which extends between a distal bend 62 and proximal bend 60 on a proximally adjacent segment of the graft. The proximal bend 60 is formed into a closed loop to form an aperture 61 for slidably entrapping the corresponding wall section 64. As used herein, the designations "proximal" and "distal" may be interchangeable when used, for example, to describe the relative position of the complementary sliding link structures on a graft. In addition, the proximal and distal designations are used sometimes herein with respect to the deployment catheter or deployment catheter direction, and other times in their anatomical sense with respect to the heart. The particular usage of these terms will be apparent to those of skill in the art in the context in which they are used herein.

Thus, referring to FIG. 34a, there is disclosed a flexible straight graft having a proximal end 50, and a distal end 52. The graft comprises a plurality of segments, such as a first segment 230, a second segment 232, a third segment 234, and a fourth segment 236. The adjacent segments can be formed separately or formed integrally such as from a single length of wire. All of the dimensions, materials and other design specifications which have been disclosed previously herein for both straight and bifurcated grafts may be provided with the sliding link design, and will therefore not be repeated. In general, however, the sliding link 220 is preferably provided on each of the connections between any two adjacent segments in a graft at which flexibility is desired, to permit the desired flexibility of the graft. For example, each of the connections between first segment 230 and second segment 232 may be provided with a sliding link 220. The connections between the intermediate segments 232 and 234 may be provided with either sliding links 220 or nonsliding links as have been disclosed elsewhere herein. The connections between the third segment 234 and fourth segment 236 may be provided with sliding links 220.

As illustrated in FIG. 34b, the sliding link 220 may slide along the wall section 64 all the way to the proximal bend 60. This range of motion may permit an undesirable degree of graft shortening or other disadvantages, and may not be necessary to achieve the radius of curvature likely to be encountered in the normal range of anatomical variation.

Referring to FIG. 34d, the axial travel of the sliding link 220 along the wall section 64 may be limited by the provision of a limit or lock 221. The lock 221 in the illustrated embodiment comprises a loop 223 of the wire from which wall section 64 is formed. The lock 221 may be provided anywhere between the distal bend 62 and the proximal bend 60, along the length of the wall section 64, depending upon the desired range of travel. The length of the wall section 64 in between the distal bend 62 and the lock 221 provides an axial compression range for the associated sliding link 220. The permitted range of travel for sliding link 220 may be varied depending upon the location of the sliding link 220 on the graft, and depending upon the desired radius of curvature for the graft in the implanted orientation.

The lock 221 may be formed as a single or double loop of the wire 64. Alternatively, the lock 221 may be separately formed and attached to the wall section 64 such as by soldering, brazing, adhesives, or by tying one or more knots in a suture or other material. A sliding link lock 221 may be provided for each sliding link 220 in a graft, or for only select sliding links 220, depending upon the desired clinical performance.

Figure 35B:
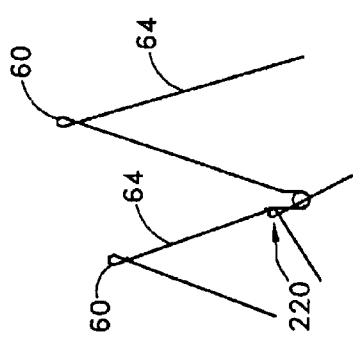
Figure 35C:
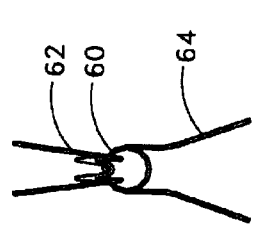
Figure 35D:
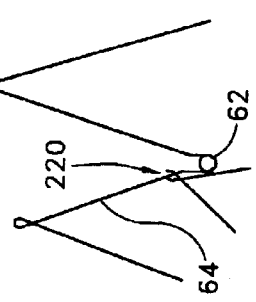
Figure 35A:
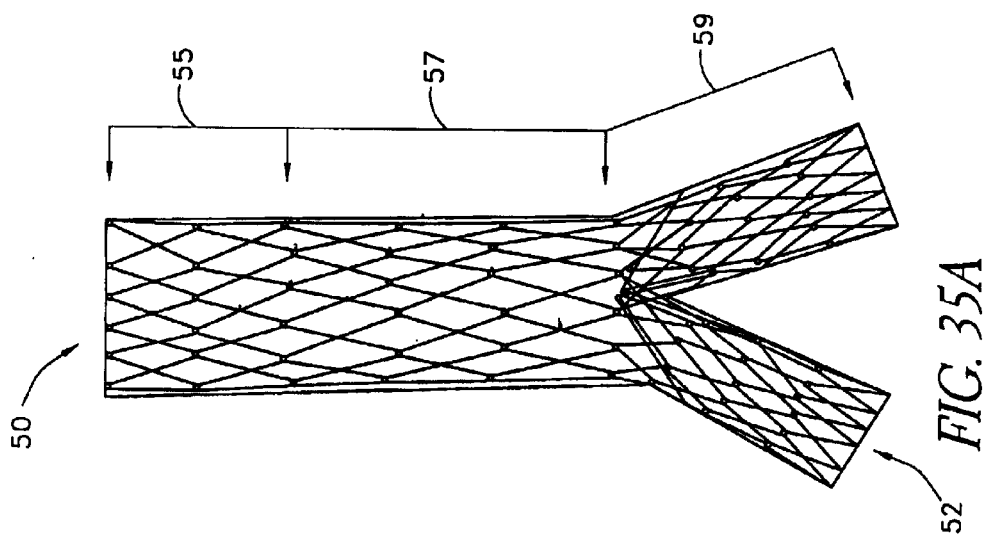
FIG. 35a is a side elevational view of a bifurcated graft which includes sliding links in accordance with the present invention.

Referring to FIGS. 35a–35d, there is illustrated an embodiment of a bifurcation graft of the present invention in which sliding links 220 are utilized to increase the lateral flexibility of the proximal and distal ends of the graft, while axially noncompressible links are utilized for the central trunk of the graft. Referring to FIG. 35a, the bifurcation graft extends between a proximal end 50 and a distal end 52. In a proximal zone 55, which may comprise two or three or more adjacent segments, the connections between each proximal bend 60 and corresponding distal bend 62 is in the form of a sliding link 220. See FIG. 35b.

Throughout an intermediate zone 57, which may comprise the third, fourth, and fifth segments of the aortic trunk portion of the graft, axially noncompressible links are provided such as those disclosed elsewhere herein. See FIG. 35c.

The distal zone 59 of the graft, which, in the context of a bifurcation graft, includes a portion or all of the right and left iliac branches, comprises sliding links 220. See FIG. 35d. This assembly allows the maintenance of a certain axial (column strength) integrity while permitting the proximal end 50 and distal end 52 to adapt to curved or otherwise unusual anatomy. Sliding links 220 may alternatively be used throughout the length of the graft, or only at the connection of the proximal-most segment and/or the distal-most segment of the graft.

Figure 36:
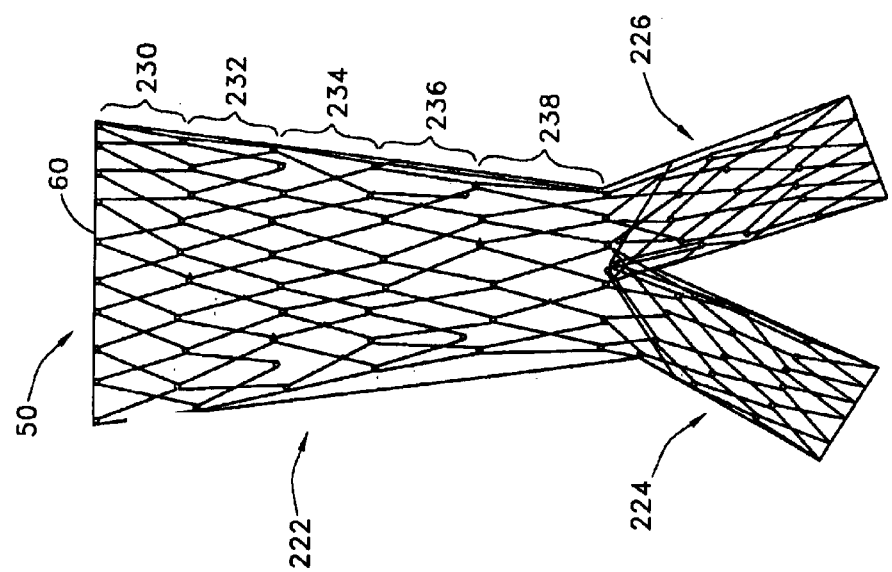
FIG. 36 is a side elevational view of a tapered bifurcated graft in accordance with the present invention.

Referring to FIG. 36, there is illustrated a tapered graft design. This design is illustrated in the context of a bifurcation graft, although it can be readily adapted for use on a straight segment graft such as that illustrated in FIG. 1. It may be readily applied to any of the bifurcation grafts disclosed herein, including, for example, those of FIGS. 17–22.

In the illustrated embodiment, an aortic trunk 222 is connected to or formed with a right iliac branch 224 and a left iliac branch 226. At least a portion of the aortic trunk 222 is tapered from a larger unconstrained expanded diameter at the proximal end 50 to a smaller unconstrained expanded diameter at the bifurcation into right iliac 224 and left iliac 226. Although FIG. 36 illustrates a relatively uniform taper throughout the length of the aortic trunk portion 222, a nonuniform taper may also be utilized. For example, the first segment 230 and second segment 232 may be provided with a taper while the third segment 234, fourth segment, and fifth segment 238 may be relatively nontapered. Any of a wide variety of alternate configurations may be devised, depending upon the desired clinical performance and intended anatomy.

In the illustrated embodiment, the first segment 230 is provided with 10 proximal bends 60. The fifth segment 238 is provided with six proximal bends 60. By successively reducing the number of proximal bends 60 (and thus the number of zig-zag components to each segment), the tapered design can be achieved. The reduction in proximal bends 60, and thus diameter of the aortic trunk portion 222, from the first segment 230 to the fifth or other last segment 238 may be such that the number of proximal bends 60 in the last segment 238 is anywhere from about 40% to about 100% of the number of proximal bends 60 in the first segment 230. In some embodiments, the last segment 238 has anywhere from about 50% to about 80% and, in certain embodiments, about 60% of the number of proximal bends 60 in the first segment 230.

The foregoing structure may be provided in any of a variety of expanded diameters. In general, for an abdominal aortic aneurysm at the bifurcation of the iliacs, the maximum expanded diameter of the first segment 230 is preferably at least about 25 mm, and in many embodiments, at least about 30 mm. In one embodiment, the expanded diameter of the first segment 230 is at least about 34 mm. The expanded diameter of the graft at the bifurcation is generally within the range of from about 22 mm to about 28 mm, and, in one embodiment, is no more than about 25 mm.

In an alternate embodiment, the tapered expanded diameter configuration may be achieved by shaping the PTFE graft into a tapered configuration which constrains expansion of the wire cage. In this embodiment, each segment of the wire cage may have the same number of proximal bends 60. However, the constraint imposed by the PTFE sleeve may produce an unnecessary and potentially undesirable bunching of the zig-zag portions of the wire frame, particularly in the area of the last segment 238.

Referring to FIG. 37, there is illustrated a graft 250 which includes a feature which may be added onto any of the embodiments disclosed previously herein, to facilitate curvature of the graft. The precurved graft 250 may be straightened for mounting on the deployment catheter, but is configured in a manner that facilitates curvature as deployed.

The precurved graft 250 includes a plurality of segments 256 as has been discussed previously. Each segment 256 comprises a plurality of proximal bends 60 and distal bends 62 separated by wall sections 64. In previous embodiments, the axial length of the wall sections 64 within a given segment 256 have been generally the same. In the embodiment of FIG. 37, however, at least one wall section 64b in a given segment 256 has a shorter length than at least one wall section 64a on the same segment 256. In a graft segment 256 having, for example, 12 wall sections 64, generally from about 2 to about 6 wall sections 64b will have a shorter length than the remainder of the wall sections 64 in that segment 256.

Upon deployment, the wall sections 64b having the shorter length will limit elongation of the graft. The opposing wall sections 64a having a longer length will allow a plurality of sliding links to extend the length of the graft thereby enabling a curve, as illustrated, having a concave side 252 and a convex side 254.

In the illustrated embodiment, the overall curvature of the graft 250 is approximately 90°. Utilizing the differential length segments 256 of the present invention, grafts or graft sections may range from linear, to curved as much as 90° or 120° or more, including as much as 180° such as for use in exotic anatomies. This may be accomplished by providing sliding links on either or both of the convex side 254 and concave side 252 of the graft 250. In one embodiment, sliding links are provided on the convex side 254 and axially fixed links are provided on the concave side 252. This minimizes intrusion of the wire cage into the central lumen on the concave side 252 of the graft 250, which may otherwise occur upon axial compression of the graft on the concave side 252.

In accordance with a further feature of the present invention, a variety of modifications may be added to any of the grafts disclosed previously herein to increase resistance to migration and/or endoleaks, such as at the anatomically proximal end of the implanted graft. Thus, referring to FIG. 38a, a graft 42 is illustrated having a plurality of proximal bends 60 on the anatomically proximal end (distal device end) of the graft 42. One or more of the proximal bends 60 is provided with a radially outwardly inclined barb 260 for increasing resistance to migration of the graft 42 within the vessel. In an embodiment having eight proximal bends 60, preferably at least two, and in some embodiments as many as four or six or all eight of the proximal bends 60 is provided with a barb 260. Generally, at least about 50% of the proximal bends 60 or associated struts will be provided with a barb or tread 260.

As illustrated, each barb 260 is integrally formed with the support structure of the graft 42, such as by forming the barb 260 as a part of the wire cage. This eliminates the need for a separately attached component, which may become disengaged and/or increases the complexity of the manufacturing process.

Referring to FIG. 38b, the barb 260 may be formed by bending the proximal bend 60 radially outwardly at a bend point 262. The radial outwardly most tip of the barb 260 may be formed with or without a loop or eye as has been discussed. The bend 262 may be formed to cause the barb 260 to extend outwardly at an angle with respect to the longitudinal axis of the graft. The angle may range, in an unconstrained form, from anywhere within the range of from about 10° to about 160° from the longitudinal axis. In the illustrated embodiment, the bend 262 produces an angle of approximately 90°.

Although not illustrated in FIG. 38a, the barbs 260 may be offset from each other or staggered with respect to the longitudinal axis of the graft 42, to minimize the collapsed profile of the graft 42 when loaded on the deployment catheter. Staggering of the barbs 260 may be accomplished by positioning the barbs 260 such that no two barbs 260 are axially aligned in a single transverse plane upon collapse of the graft 42. Alternatively, the barbs 260 may be alternated between a first transverse plane and a second transverse plane or a first, a second, and a third transverse plane as will be apparent to those of skill in the art in view of the disclosure herein. A similar staggering may be accomplished with respect to the plurality of links 258 in-between any adjacent segments in the graft, in any of the embodiments disclosed herein. This is illustrated in FIG. 38a in a stagger pattern such that about half of the links 258 in a given joint between adjacent graft segments reside in a first transverse plane and the other half reside in a second transverse plane. This permits a tighter nesting or lower crossing profile for the collapsed graft. This feature is independent of the barbs 260, and either or both feature may be incorporated into any of the preceding embodiments.

A modified barb 260 is illustrated in FIG. 38c. In this embodiment, a portion of the wall sections 264 are bent in a first, radially inwardly inclined direction and then provided with a second bend to direct the tip of the barb 260 in a radially outwardly inclined direction. Other barb configurations can be readily achieved, as will be apparent to those of skill in the art in view of the disclosure herein.

A further feature of the present invention which may be provided on any of the embodiments discussed previously herein is illustrated in FIGS. 39a–c. In accordance with this feature, an exoskeleton 264 is provided at some point on the radially outwardly facing surface of the graft fabric, to facilitate endothelialization or other biological encorporation mechanism for providing resistance to migration of the implanted graft. The exoskeleton 264 is particularly useful in an embodiment wherein the fabric of the graft resists or does not permit tissue ingrowth.

Referring to FIG. 39a, each proximal bend 60 at the anatomically proximal end of the graft is connected by a generally V- or U-shaped partial exoskeleton segment 266. The exoskeleton segment 266 may extend beyond the end of the fabric, or may be folded back on top of the fabric as illustrated in FIG. 39a. Each exoskeleton segment 266 terminates proximally in a bend 268 which may or may not include a loop or eye as has been discussed. The axial distance along the graft between the proximal bend 60 and adjacent exoskeleton bend 268 may be varied, depending upon the desired clinical performance. Generally, that axial distance is within the range of from about 1.5 cm to about 2.5 cm.

In addition, the plurality of bends 268 may be offset in the axial direction from a common transverse plane, to reduce the collapsed crossing profile of the graft as has been discussed. One or two or more of the bends 268 may be inclined radially outwardly and/or biased radially outwardly to resist migration.

A partial exoskeleton 264 may also be accomplished by leaving one or more adjacent apexes between adjacent graft segments unconnected from each other, and sliding the fabric of the graft beneath the unattached graft apex. This is illustrated, for example, in FIG. 39b. In the illustrated embodiment, alternating distal bends 62 from the anatomically proximal-most graft segment remain on the outside of the graft fabric, while the remaining half of the distal bends 62 of the proximal-most graft segment remain connected to corresponding proximal bends 60 on the second to last graft segment.

In the second to last graft segment, the unattached proximal bends 60 may reside as illustrated in FIG. 39b, or it may be extended all the way to or near the proximal end of the graft, such as illustrated in FIG. 39c.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. A tubular wire support for combination with a sheath to produce a bifurcated endoluminal prosthesis, said tubular wire support comprising:
   a main body support structure having a proximal end, a distal end and a central lumen extending therethrough, the support structure comprising at least a first and second axially adjacent tubular segments, each segment comprising a plurality of wall struts connected by proximal and distal bends;
   a first branch support structure having a proximal end, a distal end and a central lumen therethrough connected to the main body support structure;
   a second branch support structure having a proximal end, a distal end and a central lumen extending therethrough, connected to the main body support structure;
   at least two sliding links in between the first and second segments; and
   at least one lock on a wall strut between a proximal bend and a distal bend for limiting axial movement of a sliding link along that strut.

2. The tubular wire support of claim 1, wherein the main body support structure and the first and second branch support structures are self-expandable from a radially collapsed state to a radially expanded state.

3. A tubular wire support as in claim 2, wherein at least a portion of the tubular wire support has an expansion ratio of at least about 1:4.

4. The tubular wire support of claim 1, further comprising a tubular sheath on the wire support.

5. The tubular wire support of claim 4, wherein the sheath comprises a PTFE sleeve surrounding at least a central portion of the wire support.

6. The tubular wire support of claim 1, wherein each segment comprises wire formed into a series of proximal bends, a series of distal bends, and a series of struts connecting the proximal and distal bends.

7. The tubular wire support of claim 6, wherein each tubular segment comprises from about 4 proximal bends to about 12 proximal bends.

8. The tubular wire support of claim 1, wherein the first and second branch support structures are pivotably attached to the main body support structure.

9. The tubular wire support of claim 1, wherein each of the at least two sliding links comprises a loop formed by a proximal or distal bend.

10. The tubular wire support of claim 1, wherein the at least one lock comprises a loop on the wall strut.

11. A flexible self expandable graft, comprising:
    a tubular main body support structure having a proximal end and a distal end, the tubular body comprising at least a first tubular segment attached to a second tubular segment; and
    a tubular polymeric sleeve surrounding at least a portion of the graft;
    wherein each of the first and second tubular segments comprise a plurality of proximal bends and distal bends connected by struts surrounding a longitudinal axis such that a first strut is on a first side of the axis and a second strut is on a second side of the axis, opposite to the first side, and in at least one segment the first strut is shorter than the second strut such that when the vascular graft is expanded the first side includes a concave curved portion and the second side includes a convex curved portion.

12. A flexible self expandable graft as in claim 11, further comprising at least a first a second sliding link between the first and second tubular segments.

13. A flexible self expandable graft as in claim 12, wherein the first and second sliding links join opposing proximal and distal bends on the first tubular segment and the second tubular segment.

14. A flexible self expandable graft as in claim 13, comprising at least four sliding links between the first and second segments.

15. A flexible self expandable graft as in claim 13, comprising a series of struts connecting the proximal bends and distal bends within a segment to a tubular segment wall, wherein at least some of the struts are substantially linear.

16. A flexible self expandable graft as in claim 15, wherein the sliding link comprises a proximal bend or distal bend on a first segment slidably engaged with a strut on an adjacent segment.

17. A flexible self expandable graft as in claim 13, wherein each segment comprises from about 4 proximal bends to about 12 proximal bends.

18. A flexible self expandable graft as in claim 13, having at least a proximal segment, an intermediate segment and a distal segment, wherein the prosthesis is expandable from a reduced cross section to an expanded cross section.

19. A flexible self expandable graft as in claim 18, wherein at least a portion of the proximal segment is larger in cross section than the central segment when the prothesis is in the expanded cross section.

20. A flexible self expandable graft as in claim 13, wherein the sleeve comprises a tubular PTFE sleeve surrounding at least a portion of the prosthesis.

21. A flexible self expandable graft as in claim 11, comprising at least four segments.

22. An endoluminal prosthesis, comprising at least one elongate flexible wire, formed into a plurality of axially adjacent tubular segments spaced along an axis, each tubular segment comprising a zig-zag section of wire, having a plurality of proximal bends and distal bends, at least one of the plurality of proximal bends and plurality of distal bends having loops thereon, and a tubular polymeric sleeve carried by the prosthesis, wherein the prosthesis is radially compressible into a first, reduced cross sectional configuration for implantation into a body lumen, and self expandable to a second, enlarged cross sectional configuration at a treatment site in a body lumen, and wherein at least a first portion of wire in one tubular segment is positioned on a radially outwardly facing surface of the sleeve and a radially inwardly facing surface of the sleeve is in contact with a second portion of wire.

23. An endoluminal prosthesis as in claim 22, comprising at least three segments formed from said wire.

24. An endoluminal prosthesis as in claim 22, wherein the prosthesis has a proximal end and a distal end, and at least one of the proximal end and distal end are expandable to a larger diameter than a central section of the prosthesis in an unconstrained expansion.

25. An endoluminal prosthesis as in claim 22, wherein the prosthesis has an expansion ratio of at least about 1:4.

26. An endoluminal prosthesis as in claim 25, wherein the prosthesis has an expansion ratio of at least about 1:5.

27. An endoluminal prosthesis as in claim 22, wherein the prosthesis has an expanded diameter of at least about 20 mm in an unconstrained expansion, and the prosthesis is implantable using a catheter no greater than about 20 French.

28. A prosthesis as in claim 27, wherein the prosthesis has an expanded diameter of at least about 25 mm, and is implantable on a delivery device having a diameter of no more than about 20 French.

29. An endoluminal prosthesis as in claim 22, comprising at least six proximal ends on a distal segment, wherein at least three of the proximal bends reside on the outside of the tubular sleeve and the remainder of the proximal bends on the distal segment are positioned on the inside of the tubular sleeve.

30. An endoluminal prosthesis as in claim 29, wherein the proximal bends on the inside of the tubular sleeve are connected to distal bends on a proximal segment.

31. An endoluminal prosthesis as in claim 22, wherein the second portion of wire is on a second tubular segment that is axially adjacent to the tubular segment containing the first portion of wire.

32. A tubular wire support for a bifurcated endoluminal prosthesis, said wire support comprising:

a main body support structure having a proximal end, a distal end and a central lumen extending along a longitudinal axis therethrough;

a first branch support structure having a proximal end, a distal end and a central lumen therethrough, wherein the distal end of the first branch support structure is connected to the proximal end of the main body support structure;

a second branch support structure having a proximal end, a distal end and a central lumen extending therethrough wherein the distal end of the second branch support structure is connected to the proximal end of the main body support structure, wherein the wire in each support structure is formed into a plurality of segments, each segment comprising a series of proximal bends, a series of distal bends, and a series of struts connecting the proximal and distal bends; and a plurality of radially outwardly extending barbs on the main body, said barbs being integrally formed on the wire support by bending a proximal or distal bend radially outwardly at a bend point;

wherein the main body support structure and the first and second branch support structure are self-expandable from a radially collapsed state to a radially expanded state.

33. The tubular wire support of claim 32, further comprising a tubular sheath on the wire support.

34. The tubular wire support of claim 33, wherein the sheath comprises a PTFE sleeve surrounding at least a central portion of the wire support.

35. The tubular wire support of claim 32 wherein each tubular segment comprises from about 4 proximal bends to about 12 proximal bends.

* * * * *

UNITED STATES PATENT AND TRADEMARK OFFICE
CERTIFICATE OF CORRECTION

PATENT NO. : 6,733,523 B2
DATED : May 11, 2004
INVENTOR(S) : Samuel M. Shaolian et al.

It is certified that error appears in the above-identified patent and that said Letters Patent is hereby corrected as shown below:

Column 30,
Line 42, delete "a" insert -- and --.
Line 53, after "to" insert -- form --.

Column 31,
Line 1, delete "prothesis" insert -- prosthesis --.
Line 44, delete "ends" insert -- bends --.

Column 32,
Line 24, after "structure", delete "," insert -- ; --.

Signed and Sealed this

Thirteenth Day of December, 2005

JON W. DUDAS
*Director of the United States Patent and Trademark Office*